(12) United States Patent
Doyle et al.

(10) Patent No.: US 9,310,361 B2
(45) Date of Patent: Apr. 12, 2016

(54) MULTIFUNCTIONAL ENCODED PARTICLES FOR HIGH-THROUGHPUT ANALYSIS

(75) Inventors: Patrick S. Doyle, Boston, MA (US); Daniel C. Pregibon, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 34 days.

(21) Appl. No.: 13/083,496

(22) Filed: Apr. 8, 2011

(65) Prior Publication Data

US 2011/0263747 A1 Oct. 27, 2011

Related U.S. Application Data

(62) Division of application No. 11/867,217, filed on Oct. 4, 2007, now Pat. No. 7,947,487.

(60) Provisional application No. 60/849,651, filed on Oct. 5, 2006.

(51) Int. Cl.
*C12Q 1/68* (2006.01)
*G01N 33/543* (2006.01)
(Continued)

(52) U.S. Cl.
CPC .... *G01N 33/54366* (2013.01); *G01N 33/54313* (2013.01); *G01N 33/582* (2013.01); *B01J 2219/005* (2013.01); *B01J 2219/0074* (2013.01); *B01J 2219/00545* (2013.01); *B01J 2219/00549* (2013.01); *B01J 2219/00576* (2013.01); *B01J 2219/00596* (2013.01); *B01J 2219/00722* (2013.01); *B01J 2219/00725* (2013.01); *B01J 2219/00743* (2013.01); *B01L 3/5027* (2013.01); *Y10S 977/704* (2013.01);
(Continued)

(58) Field of Classification Search
CPC . G01N 33/54366; B01L 3/5027; C12Q 1/689
USPC .................................. 435/6.1, 287.2
See application file for complete search history.

(56) References Cited

U.S. PATENT DOCUMENTS 3,687,808 A   8/1972   Merigan et al.
4,152,496 A * 5/1979   Barrett et al. ................... 521/54
(Continued)

FOREIGN PATENT DOCUMENTS

AU   2006331607 A1   7/2007
GB   2388652 B      3/2005
(Continued)

OTHER PUBLICATIONS

Armstrong, B. et al. "Cytometry". 40, No. 2, 102-108 (2000).
(Continued)

*Primary Examiner* — Betty Forman
(74) *Attorney, Agent, or Firm* — Choate, Hall & Stewart LLP; Fangli Chen; Meaghan Bychowski

(57) ABSTRACT

Method for making multifunctional particles. The method includes flowing a first monomer stream loaded with a fluorescent entity along a microfluidic channel and flowing a second monomer stream loaded with a probe adjacent to the first monomer stream along the microfluidic channel. The monomer streams are polymerized to synthesize particles having a fluorescent, graphically encoded region and a probe-loaded region.

18 Claims, 11 Drawing Sheets

(51) Int. Cl.
*G01N 33/58* (2006.01)
*B01L 3/00* (2006.01)

(52) U.S. Cl.
CPC .......... *Y10S 977/712* (2013.01); *Y10S 977/733* (2013.01); *Y10S 977/795* (2013.01)

(56) References Cited

U.S. PATENT DOCUMENTS

| | | | |
|---|---|---|---|
| 4,194,066 A | 3/1980 | Kaetsu et al. | |
| 4,683,194 A | 7/1987 | Saiki et al. | |
| 4,743,545 A | 5/1988 | Torobin | |
| 4,845,205 A | 7/1989 | Huynh Dinh et al. | |
| 4,929,400 A | 5/1990 | Rembaum et al. | |
| 4,981,957 A | 1/1991 | Lebleu et al. | |
| 5,117,357 A | 5/1992 | Inoue | |
| 5,118,800 A | 6/1992 | Smith et al. | |
| 5,130,302 A | 7/1992 | Spielvogel et al. | |
| 5,134,066 A | 7/1992 | Rogers et al. | |
| 5,175,273 A | 12/1992 | Bischofberger et al. | |
| 5,210,015 A | 5/1993 | Gelfand et al. | |
| 5,319,080 A | 6/1994 | Leumann | |
| 5,359,044 A | 10/1994 | Cook et al. | |
| 5,367,066 A | 11/1994 | Urdea et al. | |
| 5,393,878 A | 2/1995 | Leumann | |
| 5,432,272 A | 7/1995 | Benner | |
| 5,446,137 A | 8/1995 | Maag et al. | |
| 5,457,187 A | 10/1995 | Gmeiner et al. | |
| 5,459,255 A | 10/1995 | Cook et al. | |
| 5,466,786 A | 11/1995 | Buhr et al. | |
| 5,484,908 A | 1/1996 | Froehler et al. | |
| 5,502,177 A | 3/1996 | Matteucci et al. | |
| 5,514,785 A | 5/1996 | Van Ness et al. | |
| 5,519,134 A | 5/1996 | Acevedo et al. | |
| 5,525,711 A | 6/1996 | Hawkins et al. | |
| 5,552,540 A | 9/1996 | Haralambidis | |
| 5,567,811 A | 10/1996 | Misiura et al. | |
| 5,576,427 A | 11/1996 | Cook et al. | |
| 5,587,469 A | 12/1996 | Cook et al. | |
| 5,591,722 A | 1/1997 | Montgomery et al. | |
| 5,594,121 A | 1/1997 | Froehler et al. | |
| 5,596,091 A | 1/1997 | Switzer | |
| 5,597,909 A | 1/1997 | Urdea et al. | |
| 5,610,300 A | 3/1997 | Altmann et al. | |
| 5,614,617 A | 3/1997 | Cook et al. | |
| 5,627,053 A | 5/1997 | Usman et al. | |
| 5,639,873 A | 6/1997 | Barascut et al. | |
| 5,645,985 A | 7/1997 | Froehler et al. | |
| 5,646,265 A | 7/1997 | McGee | |
| 5,658,873 A | 8/1997 | Bertsch-Frank et al. | |
| 5,668,268 A | 9/1997 | Tang et al. | |
| 5,670,633 A | 9/1997 | Cook et al. | |
| 5,677,196 A | 10/1997 | Herron et al. | |
| 5,681,941 A | 10/1997 | Cook et al. | |
| 5,700,920 A | 12/1997 | Altmann et al. | |
| 5,763,588 A | 6/1998 | Matteucci et al. | |
| 5,792,747 A | 8/1998 | Schally et al. | |
| 5,830,653 A | 11/1998 | Froehler et al. | |
| 5,876,924 A | 3/1999 | Zhang et al. | |
| 5,879,900 A | 3/1999 | Kim et al. | |
| 5,916,539 A | 6/1999 | Pilgrimm | |
| 5,945,526 A | 8/1999 | Lee et al. | |
| 5,981,180 A | 11/1999 | Chandler et al. | |
| 6,005,096 A | 12/1999 | Matteucci et al. | |
| 6,150,102 A | 11/2000 | Mills, Jr. et al. | |
| 6,159,739 A | 12/2000 | Weigl et al. | |
| 6,251,303 B1 | 6/2001 | Bawendi et al. | |
| 6,319,426 B1 | 11/2001 | Bawendi et al. | |
| 6,322,901 B1 | 11/2001 | Bawendi et al. | |
| 6,344,316 B1 | 2/2002 | Lockhart et al. | |
| 6,376,742 B1 | 4/2002 | Zdrahala et al. | |
| 6,423,551 B1 | 7/2002 | Weiss et al. | |
| 6,426,513 B1 | 7/2002 | Bawendi et al. | |
| 6,444,143 B2 | 9/2002 | Bawendi et al. | |
| 6,488,872 B1 | 12/2002 | Beebe et al. | |
| 6,532,061 B2 | 3/2003 | Ortyn et al. | |
| 6,576,291 B2 | 6/2003 | Bawendi et al. | |
| 6,592,821 B1 | 7/2003 | Wada et al. | |
| 6,649,138 B2 | 11/2003 | Adams et al. | |
| 6,815,064 B2 | 11/2004 | Treadway et al. | |
| 6,934,408 B2 | 8/2005 | Frost et al. | |
| 7,255,994 B2 | 8/2007 | Lao | |
| 7,319,003 B2 | 1/2008 | Cantor et al. | |
| 7,438,792 B2 | 10/2008 | Mathies et al. | |
| 7,709,544 B2 * | 5/2010 | Doyle et al. | 522/3 |
| 7,947,487 B2 * | 5/2011 | Doyle et al. | 435/283.1 |
| 8,034,629 B2 | 10/2011 | Chapin et al. | |
| 8,232,049 B2 | 7/2012 | Nilsen et al. | |
| 8,535,644 B2 | 9/2013 | Haghgooie et al. | |
| 8,609,337 B2 | 12/2013 | Pregibon et al. | |
| 8,647,742 B2 | 2/2014 | Dendukuri et al. | |
| 2001/0023078 A1 | 9/2001 | Bawendi et al. | |
| 2002/0001813 A1 | 1/2002 | Taylor et al. | |
| 2002/0004573 A1 | 1/2002 | Domschke et al. | |
| 2002/0056945 A1 | 5/2002 | Gelbart | |
| 2002/0155490 A1 | 10/2002 | Skinner et al. | |
| 2002/0165198 A1 | 11/2002 | Singh et al. | |
| 2002/0197614 A1 | 12/2002 | Weir et al. | |
| 2003/0032203 A1 | 2/2003 | Sabatini et al. | |
| 2003/0045597 A1 | 3/2003 | Randolph et al. | |
| 2003/0049629 A1 | 3/2003 | Edman et al. | |
| 2003/0059764 A1 * | 3/2003 | Ravkin et al. | 435/4 |
| 2003/0108900 A1 | 6/2003 | Oliphant et al. | |
| 2003/0143604 A1 | 7/2003 | Storhoff et al. | |
| 2004/0005352 A1 | 1/2004 | Lopez et al. | |
| 2004/0038408 A1 | 2/2004 | Abbott et al. | |
| 2004/0043506 A1 | 3/2004 | Haussecker et al. | |
| 2004/0069857 A1 | 4/2004 | Leblans et al. | |
| 2004/0110141 A1 | 6/2004 | Pusey et al. | |
| 2004/0126820 A1 | 7/2004 | Chan et al. | |
| 2004/0209376 A1 * | 10/2004 | Natan et al. | 436/56 |
| 2004/0210289 A1 | 10/2004 | Wang et al. | |
| 2004/0248163 A1 | 12/2004 | Kramer et al. | |
| 2005/0043428 A1 | 2/2005 | Caneba et al. | |
| 2005/0147973 A1 | 7/2005 | Knott | |
| 2005/0172476 A1 | 8/2005 | Stone et al. | |
| 2005/0196702 A1 | 9/2005 | Bryant et al. | |
| 2005/0214737 A1 | 9/2005 | Dejneka et al. | |
| 2005/0214825 A1 | 9/2005 | Stuelpnagel | |
| 2005/0233318 A1 | 10/2005 | Chee et al. | |
| 2006/0019258 A1 | 1/2006 | Yeakley | |
| 2006/0094025 A1 | 5/2006 | Getts et al. | |
| 2006/0121122 A1 | 6/2006 | Nakajima et al. | |
| 2006/0147924 A1 | 7/2006 | Ramsing et al. | |
| 2006/0201390 A1 | 9/2006 | Lahann et al. | |
| 2006/0228386 A1 | 10/2006 | Stephens et al. | |
| 2006/0228735 A1 | 10/2006 | Bobrow et al. | |
| 2006/0228742 A1 | 10/2006 | Hashmi et al. | |
| 2007/0003940 A1 | 1/2007 | Wang | |
| 2007/0037195 A1 * | 2/2007 | Ho | 435/6 |
| 2007/0054119 A1 | 3/2007 | Garstecki et al. | |
| 2007/0065844 A1 | 3/2007 | Golub et al. | |
| 2007/0105972 A1 | 5/2007 | Doyle et al. | |
| 2008/0026394 A1 | 1/2008 | Labgold et al. | |
| 2008/0176216 A1 | 7/2008 | Doyle et al. | |
| 2008/0182239 A1 | 7/2008 | Mullinax et al. | |
| 2008/0213912 A1 | 9/2008 | Randall et al. | |
| 2008/0234144 A1 | 9/2008 | Ho et al. | |
| 2008/0305481 A1 | 12/2008 | Whitman et al. | |
| 2009/0036316 A1 | 2/2009 | Drmanac | |
| 2009/0061424 A1 | 3/2009 | Chen | |
| 2009/0063095 A1 | 3/2009 | Bagwell | |
| 2009/0201504 A1 | 8/2009 | Ho et al. | |
| 2010/0129855 A1 | 5/2010 | Kataoka et al. | |
| 2011/0129941 A1 * | 6/2011 | Kumacheva et al. | 436/180 |

FOREIGN PATENT DOCUMENTS

| | | |
|---|---|---|
| JP | 54074886 A | 6/1979 |
| JP | 11 118819 A | 4/1999 |
| WO | WO-98/39352 A1 | 9/1998 |
| WO | WO-99/14226 A2 | 3/1999 |
| WO | WO-00/49385 A2 | 8/2000 |
| WO | WO-00/74927 A1 | 12/2000 |

(56) References Cited

FOREIGN PATENT DOCUMENTS

| | | |
|---|---|---|
| WO | WO-01/16152 A2 | 3/2001 |
| WO | WO-2004026457 A1 | 4/2004 |
| WO | WO-2005/103106 A1 | 11/2005 |
| WO | WO-2004/076056 A3 | 12/2006 |
| WO | WO-2007/050704 A2 | 5/2007 |
| WO | WO-2007/071062 A1 | 6/2007 |
| WO | WO-2007/075894 A2 | 7/2007 |
| WO | WO-2007/050704 A3 | 8/2007 |
| WO | WO-2007/075894 A3 | 1/2008 |
| WO | WO-2008/063758 A2 | 5/2008 |
| WO | WO-2008/124423 A2 | 10/2008 |
| WO | WO-2009/002225 A2 | 12/2008 |
| WO | WO-2009/021923 A1 | 2/2009 |
| WO | WO-2009/029742 A1 | 3/2009 |
| WO | WO-2009/046149 A1 | 4/2009 |
| WO | WO-2011/156432 A2 | 12/2011 |

OTHER PUBLICATIONS

Battersby, B.J. et al. "J. Am. Chem. Soc." 122, 2138 (2000).
Beebe et al. "Functional Hydrogel Structures for Autonomous Flow Control Inside Microfluidic Channels". Nature, 200, 404: 588-590.
Braeckmans, Kevin et al. "Nature Materials", 2, No. 3, 169 (2003).
Braeckmans, Kevin et al. "Nat. Rev. Drug Discov.", 1, 227 (2002).
Braeckmans, K. et al. "Nat. Matter" 2, 169 (2003).
Cruise, G.M. et al. "Biomaterials" 19, 1287 (1998).
Cunin, F. et al. "Nat. Mater." 1, 39 (2002).
De Jager W. et al. "Methods" 38, 294 (2006).
Dendukuri, D. et al. "Nat. Mater." 5, 365 (2006).
Dunbar, S.A. et al. "J. Microbiol. Methods" 53, 245 (2003).
Evans, M. et al. "Assay Drug Dev. Technol." 1, 199 (2003).
Eyal, and Quake. "Electrophoresis" 23, 2653 (2002).
Fan, J.B. et al. "Nat. Rev. Genet." 7, 632, (2006).
Ferguson, J.A. et al. "Anal Chem." 72, 5618 (2000).
Fenniri, S. et al. "J. Am. Chem. Soc." 125, 10546 (2003).
Finkel, N.H. et al. "Anal Chem." 76, 353A (2004).
Fodor, S. P. et al. "Nature" 364, 555 (1993).
Fulton, R.J. et al. "Clin. Chem", 43, 1749 (1997).
Gershon, D. "Nature", 416, 885 (2002).
Han, M. et al. "Nat Biotechnol." 19, 631 (2001).
Hergt, R. et al. "IEEE Trans. Magn." 34, 3745 (1998).
Hunt, H.C. et al. "Microfluidics and Nanofluidics" 4, No. 1-2, 53-79 (2008).
International Search Report for PCT/US2007/080426, mailed Sep. 30, 2008.
Irizarry, R.A. et al. "Bioinformatics" 22, 789 (2006).
Kohara, Y. et al. "Nucleic Acids Res." 30, e87 (2002).
McClain et al. "Anal. Chem." 75, 5646 (2003).
McHugh, T. M. et al. "J. Clin. Microbial" 26, 1957 (1988).
Mellott, M.B. "Biomaterials" 22, 929 (2001).
Moran, E. J. et al. "J. Am. Chem. Soc." 117, 10787 (1995).
Nicewarner-Pena et al. "Science" 294, 137 (2001).
Nicolaou, K. C. et al. "Agnew Chem. Int. Ed." 34, 2289 (1995).
Nie et al "Janus and Ternanry Particles Generated by Microfluidic Synthesis: Design, Synthesis and Self-Assembly" J. Am. Chem. Soc. Jul. 2006, 128: 9408-9412.
Nolan, J.P. et al. "Trends Biotechnol." 20, 9 (2002).
Pearce, M.E. et al. "Pharmaceutical Research" 24 No. 12, 2335 (2007).
Pregibon, D.C. et al. "Langmuir" 22, 5122 (2006).
Pregibon, Daniel C. et al. "Science" 315, 1393 (2007).
Roh et al "Biphasic Janus Particles with Nanoscale Anisotropy" Natuer Materials, Oct. 2005, 4: 759-763.
Service, R.F. "Science" 270, 577 (1995).
Sha, M. Y. et al. "Anal Bioanal. Chem." 384, 658 (2006).
Simonnet, C. et al. "Anal. Chem." 78, 5653 (2006).
Sinclair et al. "App. Optics" 43, 2079 (2004).
Stevens, P.W. et al. "Nucleic Acids Res." 27, 1719 (1999).
Su, X. et al. "Nano Lett." 5, 49 (2005).
Rehman, F.N. et al. "Nucleic Acids Res." 27, 649 (1999).
Rubina, A.Y. et al. "Biotechniques" 34, 1008 (2003).
Vaino, A. R. et al. "Natl. Acad. Sc". U.S.A. 97, 7692 (2000).
Vasiliskov, A.V. et al. "Biotechniques" 27, 592 (1999).
Wang, et al. "Lab Chip" 4, 625 (2004).
Written Opinion of the International Searching Authority for PCT/US2007/080426, mailed Sep. 30, 2008.
Xu, H. et al. "Nucleic Acids Res.", 31, e43 (2003).
Zhao, X.W. et al. "Chem. Matter" 18, 2443 (2006).
Zhi, Z. L. et al. "Anal Chem" 75, 4125 (2003).
Australian Patent Examination Report No. 1 from AU2007324117, dated Aug. 15, 2012, 4 pages.
Fotin et al., Parallel thermodynamic analysis of duplexes on oligodeoxyribonucleotide microchips, Nucleic Acids Research, 1998, 26(6): 1515-1521.
Sorokin et al., Kinetics of hybridization on surface oligonucleotide microchips: Theory, experiment, and comparison with hybridization on gel-based microchips, Journal of Biomolecular Structure & Dynamics, 2006, 24(1): 57-66.
Ciba Formulators Guide for Coatings—Photoinitiators for UV Curing. Ciba Specialty Chemicals. Available on the web Sep. 2003 at http://www.mufong.com.tw/Ciba/ciba_guid/photo_uv_2.pdf.
Dendukuri et al., Controlled Synthesis of Nonspherical Microparticles Using Microfluids, Langmuir, 2005, 21: 2113-2116.
Fialkowski et al., Self-assembly of Polymerc Microspheres of Complex Internal Structures, Nature Materials, 2005, 4, 93-97.
Hillborg et al., Crosslinked Polydimethylsilozane Exposed to Ocygen Plasma Studied by Neutron Reflectrometry and Other Surface Specific Techniques, Polymer, 2000, 41(18): 6851-6863.
Jo et al., Three-Dimensional Micro-Channel Fabrication in Polydimethylsiloxane (PDMS) Elastomer, Journal of Microelctromechanical Systems, 2000, 9(1): 76-81.
Kenis et al., Microfabrication Inside Capillaries Using Multiphase Laminar Flow Patterning, Science, 1999, 285: 83-85.
Kim et al., Hydrodynamic Fabrication of Polymeric Barcoded Strips as Components for ParalletII Bio-Analysis and Programmable Microactuation, Lab Chip, 2005, 5: 1168-1172.
Millman et al., Anisotropic Particle Synthesis in Dielectrophoretically Controlled Microdroplet Reactors, Nature Materials 2005, 4: 98-102.
Mukhoadhyay, Microparticles of all Shapes and Chemistries, Analysical Chemistry, 2006, 4247.
Nisisako et al., Synthesis of Monodisperse Bicolored Janus Particles with Electrical Anisotropy Using a Microfluidic Co-Flow System, Adv. Mater., 2006, 18: 1152-1156.
Perro et al., Design and Sythesis of Janus Micro- and Nonoparticles, Journal of Materials Chemistry, 2005, 15: 3745-3760.
Research Highlights, Lab Chip, 2006, 6: 707-709.
Research Highlights, Nature, 2006, 440: 848.
Rolland et al., Direct Fabrication and Harvesting of Monodisperse, Shape-Specific Nanobiomaterials, J. Am. Chem. Soc, 2005, 127: 10096-10100.
Shiku et al., Oxygen Permeability of Surface-Modified Poly(dimethylsiloxane) Charactarized by Scanning Electrochemical Microscopy, Chemistry Letters, 2006, 35(2) 234-235.
Sugiura et al., Preparation of Monodispersed Polymeric Microspheres over 50 Micron Employing Microchanncel Emulsification, Ind. Eng. Chem. Res., 2002, 4043-4047.
International Search Report for PCT/US2006/041668, dated Jun. 18, 2007, 5 pages.
Written Opinion for PCT/US2006/041668, dated Jun. 18, 2007, 9 pages.
Albretsen et al., Applications of Magnetic Beads with Covalently Attached Oligonucleotides in Hybridization, Analytical Biochemistry, 189; 40-50 (1990).
Bong et al., Magnetic Barcoded Hydrogel Microparticles for Multiplexed Detection, Langmuir Article, American Chemical Society, 26(11):8008-8014 (2010).
Bong, K. et al., Lock Release Lithography for 3D and Composite Microparticles, Lab on a Chip 9(70):863-866 (2009).
Bullard et al., Direct comparison of nick-joining activity of the nucleic acid ligases from bacteriophage T4, Biochem J, 398; 135-144 (2006).

(56) References Cited

OTHER PUBLICATIONS

Canadian Office Action for Application No. 2.665.536, dated Dec. 19, 2013, 2 pages.
Castoldi et al., A sensitive array for microRNA expression profiling (miChip) based on locked nucleic acids (LNA), RNA 12(5):913-20 (2006).
Chapin et al., Ultrasensitive Multiplexed MicroRNA Quantification on Encoded Gel Microparticles Using Rolling Circle Amplification, Analytical Chemistry 83(18):7179-85 (2011).
Chapin, S.C. et al., High-throughput flow alignment of barcoded hydrogel microparticles, Lab on a Chip, 9(21): 3100-3109 (2009).
Chen et al., Pre-tension generates strongly reversible adhesion of a spatula pad on substrate, J. R. Soc. Interface 6(35):529-37 (2009).
Chen et al., Real-time quantification of microRNAs by stem-loop RT-PCR, J. Nucleic Acids Res. 33(20):e179 (2005).
Chung, S. et al., Plastic microchip flow cytometer based on 2- and 3-dimensional hydrodynamic flow focusing, Microsystem Technno. 9(8):535-533 (2003).
Chung, T. et al., Recent advances in miniaturized microfluidic flow cytometry for clinical use, Electrophersis, 28(24):4511-20 (2007).
Collins et al., A DNA polymorphism discovery resource for research on human genetic variation. Genome Res. 8(12):1229-31 (1998).
Communication pursuant to Article 94(3) EPC for EP11793064.4, 5 pages (Jul. 2, 2014).
Crooke et al., Antisense Research and Applications, 289-302 (1993).
Crosland-Taylor, P.J., A device for counting small particles suspended in a fluid through a tube, Nature, 171(4340):37-8 (1953).
Dendukuri et al., Stop-flow lithography in a microfluidic device, Lab on a Chip 7(7):818-28 (2007).
Dendukuri et al., Synthesis and self-assembly of amphiphilic polymeric microparticles, Langmuir 23(8):4669-74 (2007).
Doerr, Mutliplexing to the Max, Nature Methods, 4(5):381 (2007).
Englisch et al., Chemically Modified Oligonucleotides as Probes and Inhibitors, Angewandte Chemie International Edition, 30(6):613-722 (1991).
European Office Action, Application No. 07868371.1-1408, 5 pages, Jun. 27, 2014.
European Search Report, Application No. 11793062.8, Nov. 20, 2013, 10 pages.
Faivre M. et al., Geometrical focusing of cells in a microfluidic device: an approach to separate blood plasma, Biorheology 43(3):147-59 (2006).
Fisher et al., Photoinitiated Polymerization of Biomaterials, Annu. Rev. Mater. Res. 31:171-81 (2001).
Ghosh et al., Covalent attachments of oligonucleotides to solid supports, Nucleic Acids Research, 15; 5353-5372 (1987).
Gill et al., Encapsulation of Biologicals within Silicate, Siloxane, and Hybrid Sol-Gel Polymers: an Effecient and Generic Approach, J. Am. Chem. Soc. 120: 8587-98 (1998).
Hall et al., Integrons found in different locations have identical 5' ends but variable 3' ends, Journal of Bacteriology, 179: 6286-6294 (1994).
He, B. et al., Nanowire sensors for multiplexed detection of biomolecules, Current Opinion in Chemical Biology, Current Biology Ltd., London, GB, 12(5): 522-528 (2008).
Huh, D., et al., Microfluidics for flow cytometric analysis of cells and particles, Physiol. Meas. 26(3):R73-98 (2005).
International Search Report for PCT/US2009/061474 dated on May 28, 2009, 3 pages.
International Search Report for PCT/US2009/66778 dated on Jan. 13, 2010, 2 pages.
International Search Report for PCT/US2011/039529 dated Feb. 9, 2012, 3 pages.
International Search Report for PCT/US2011/39531 dated Feb. 23, 2012, 6 pages.
International Search Report for PCT/US2013/029854 dated Jul. 4, 2013, 4 pages.
Ju et al., Fluorescence energy transfer dye-labeled primers for DNA sequencing and analysis, Proc. Nat'l Acad. Sci., 92; 4347 (1995).

Kellar, K. et al., Multiplexed microsphere-based flow cytometric immunoassays for human cytokines, J. Immunol. Methods 279(1-2):277-85 (2003).
Kellar, K.L., et al., Multiplexed microsphere-based flow cytometric assays, Exp. Hematol. 30(11): 1227-37 (2002).
Kroschwitz, The Concise Encyclopedia of Polymer Science and Engineering, 858-9 (1990).
Lee et al., Colour-barcoded magnetic microparticles for multiplexed bioassays, Nature Materials, 9:745-749 (2010).
Lee et al., DNA-based bioanalytical microsystems for handheld device applications, Analytica Chemica 556(1):26-37 (2006).
Lee, H. et al., Colour-barcoded magnetic microparticles for multiplexed bioassays, Nature Materials, 9(9): 745-749 (2010).
Lu et al., MicroRNA expression profiles classify human cancers, Nature 435(7043):834-8 (2005).
Lund et al., Assessment of methods for covalent binding of nucleic acids to magnetic beads, DynabeadsTM and the characteristics of the bound nucletic acids in hybridization reactions, Nucleic Acids Research, 16; 10861-80 (1988).
Lyamichev et al., Invader Assay for SNP Genotyping, Methods in Molecular Biology 212:229-40 (2002).
Meade, S. et al., Multiplexed DNA Detection Using Spectrally Encoded Porous $SiO_2$ Photonic Crystal Particles, Analytical Chemistry, 81(7): 2618-2625 (2009).
Morgan, E. et al., Cytometric bead array: a multiplexed assay platform with applications in various areas of biology, Clin. Immunol. 110(3):252-66 (2004).
Nailis et al., Development and evaluation of different normalization strategies for gene expression studies in Candida albicans biofilms by real-time PCR. BMC Mol. Biol. 7:25 (2006).
Nazarenko et al., Multiplex quantitative PCR using self-quenched primers labeled with a single fluorophore, Nucleic Acids Research 30(9):e37 (2002).
Nolan T. et al., Quantification of mRNA using realtime RT-PCR, Nat. Protoc. 1(3):1559-1582 (2006).
Noor, M.R. et al., Electrical Detection of Single-Base DNA Mutation Using Functionalized Nanoparticles, Applied Physics Letters, 95(7), 4 pages (2009).
O'Connell et al., Testing of the BioSeeq (Smiths Detection Handheld PCR Instrument): Sensitivity, Specificity, and Effect of Interferents on Bacillus Assay Performance (2004).
Office Action for JP 2009-531603, dated Mar. 8, 2013, 5 pages.
Panda et al., Stop-flow lithography to generate cell-laden microgel particles, Lab on a Chip 8(7):1056-61 (2008).
Peck et al., A Method for High-Throughput Gene Expression Signature Analysis, Genome Biology, 7(7):R61 (2006).
Pregibon and Doyle, Optimization of encoded hydrogel particles for nucleic acid quantification, Anal. Chem. 81(12):4873-81 (2009).
Ray UK Startup DNA Electronics Developing Handheld Device to Detect Genetic Risk for Drug AEs, Pharmacogenomics Reporter (2009).
Stears et al., A novel, sensitive detection system for high-density microarrays using dendrimer technology, Physiol Genomics 3: 93-9 (2000).
Stockton et al., Multiplex PCR for typing and subtyping influenza and respiratory syncytial viruses, J. Clin. Microbiol 36(10):2990-5 (1998).
Tamura et al., MEGA5: molecular evolutionary genetics analysis using maximum likelihood, evolutionary distance, and maximum parsimony methods, Mol. Biol. Evol. 28(10):2731-9 (2011).
Van Doorn et al., Quantitative Multiplex Detection of Plant Pathogens Using a Novel Ligation Probe-Based System coupled with Universal, High-Throughput Real-Time PCR on OpernArrays(TM), BMC Genomics 8(1): 1-14 (2007).
Wang et al., Direct and sensitive miRNA profiling from low-input total RNA, RNA 13(1):151-9 (2007).
Watson et al., Cystic fibrosis population carrier screening: 2004 revision of American College of Medical Genetics mutation panel, Genet. Med. 6(5):387-91 (2004).
Wessensteiner et al., PCR Technology: Current Innovations (2007).
Wolf et al., Rapid hybridization kinetics of DNA attached to submicron latex particles, Nucleic Acids Research, 15; 2911-26 (1987).

(56) References Cited

OTHER PUBLICATIONS

Written Opinion for PCT/US2009/66778, dated on Jan. 13, 2010, 9 pages.
Written Opinion for PCT/US2011/039529, dated Feb. 9, 2012, 5 pages.
Written Opinion for PCT/US2011/39531, dated Feb. 23, 2012, 8 pages.
Written Opinion for PCT/US2013/029854, dated Jul. 4, 2013, 8 pages.
Yang, A. et al., Hydrodynamic focusing investigation in a micro-flow cytometer, Biomed. Microdevices 9(2):113-22 (2007).
Zhu et al., High-Sensitivity Capillary Electrophoresis of Double-Stranded DNA Fragments Using Monomeric and Dimeric Fluorescent Intercalating Dyes, Anal. Chem., 66; 1941-8 (1994).
Pregibon, D.C., Enabling Technologies for Multiplexed Biomolecule Analysis and Cell Sorting, Massachusetts Institute of Technology, Department of Chemical Engineering, 1-122 (May 23, 2008).

\* cited by examiner

▨ Orientation Indicators
☐ Coding Benefits
▨ Analyze Detection Region
↔ Reading Lanes

MULTIFUNCTIONAL ENCODED PARTICLES FOR HIGH-THROUGHPUT ANALYSIS

This application is a divisional of U.S. patent application Ser. No. 11/867,217, filed Oct. 4, 2007, now U.S. Pat. No. 7,947,487 which claims priority to Provisional Application Ser. No. 60/849,651 filed on Oct. 5, 2006, the contents of each of which are incorporated herein by reference in their entirety.

SEQUENCE LISTING

In accordance with 37 C.F.R. §1.52(e)(5), a Sequence Listing in the form of a text file (entitled "Sequence_Listing," created on Jun. 9, 2011, and 1 kilobytes) is incorporated herein by reference in its entirety.

BACKGROUND OF THE INVENTION

This invention relates to high-throughput biomolecule analysis and more particularly to a system that utilizes multifunctional encoded particles.

The ability to quantify multiple proteins, cytokines, or nucleic acid sequences in parallel using a single sample allows researchers and clinicians to obtain high-density information with minimal assay time, sample volume, and cost. Such multiplexed analysis is accompanied by several challenges, including molecular encoding and the need to retain assay sensitivity, specificity, and reproducibility with the use of complex mixtures. There are two broad classes of technologies used for multiplexing: planar arrays (1-3) and suspension (particle-based) arrays (4-21), both of which have application-specific advantages. Numbers in parentheses refer to the references appended hereto, the contents of all of which are incorporated herein by reference. Planar arrays, such as DNA and protein microarrays, are best suited for applications requiring ultra-high-density analysis. In comparison, suspension arrays benefit from solution kinetics, ease of assay modification, higher sample throughput, and better quality control by batch synthesis (22). Although particle-based arrays have been used for high-density genotyping applications (23), they are most favorable over microarrays when detecting a modest number of targets over large populations or when rapid probe-set modification is desired. Whereas planar arrays rely strictly on positional encoding, suspension arrays have used a great number of encoding schemes that can be classified as spectrometric (4-11), graphical (12-16), electronic (17-19), or physical (20, 21).

Spectrometric encoding uses specific wavelengths of light or radiation [including fluorophores (4-7), chromophores (8), photonic structures (9), and Raman tags (10, 11)] to identify a species. Fluorescence-encoded microbeads (4-7) can be rapidly processed by using conventional flow cytometry [or on fiber-optic arrays (24)], making them a popular platform for multiplexing. However, there are several disadvantages of using multiple fluorescent signals as means of barcoding, including (i) the limited barcodes achievable (typically ~100) because of spectral overlap, (ii) the lack of portability for bulky flow cytometers, (iii) added cost with each fluorescent exciter and detector needed, and (iv) potential interference of encoding fluorescence with analyte-detection fluorescence. For these reasons, single-fluorescence methods exist that use graphical techniques to spatially embed barcodes on microcarriers.

Graphical barcodes rely on the patterning of optical elements on a microcarrier; some examples include striped rods (12, 13), ridged particles (14), and dot-patterned particles (14, 15). The chemistries used to fabricate such particles (metallic or photoresist) require additional coupling chemistries to conjugate biomolecules to the surface, and, in the case of striped rods, each metallic pattern needs to be generated one batch at a time. Typically, the patterns on these particles can only be distinguished if the fluorescence of the target signal is sufficiently high. Another graphical method for microcarrier encoding is the selective photobleaching of codes into fluorescent beads (16). In this method, both particle synthesis and decoding are time-consuming, making it an unlikely candidate for high-throughput analysis. A method that eliminates fluorescence altogether uses radio frequency memory tags (17-19). This approach is very powerful because it allows for nearly unlimited barcodes (>$10^{12}$) and decouples the barcoding scheme from analyte quantification (fluorescence), but the synthesis of any appreciable number (thousands or millions) of these electronic microchip-based carriers may prove to be expensive and slow. These and several other methods developed for multiplexed analysis have been thoroughly reviewed elsewhere (25, 26).

SUMMARY OF THE INVENTION

In one aspect, the invention is a method for making multifunctional particles including flowing a first monomer stream loaded with a fluorescent entity along a microfluidic channel. A second monomer stream loaded with a probe adjacent to the first monomer stream flows along the microfluidic channel. The two monomer streams are polymerized to synthesize particles having a fluorescent, graphically encoded region and a probe-loaded region. There may be more than two monomer streams if desired. In a preferred embodiment, the polymerizing step includes exposing the first and second monomer streams to ultraviolet light transmitted through a photomask to create the encoded region. The encoded region may include a plurality of open and closed coding elements. It is preferred that the coding elements be arranged in a two-dimensional grid. An exemplary grid includes 20 coding elements. The grid may also include at least one orientation indicator. In another preferred embodiment, the polymerizing step produces more than one probe-loaded region.

In a preferred embodiment, the ultraviolet light is focused by a microscope objective. A suitable material for the first and second monomer streams is poly(ethylene glycol)diacrylate. The first and second monomer streams preferably include a photoinitiator.

In yet another aspect, the invention is a multifunctional particle including a first graphically encoded region and a second region loaded with a probe.

In yet another aspect, the invention is a high-throughput screening system including multifunctional particles having a graphically encoded region and a probe-loaded region. A flow-focusing microfluidic device is provided to align and read the particles.

DESCRIPTION OF THE PREFERRED EMBODIMENTS

We introduce a technique that overcomes many of these multiplexing limitations. By exploiting laminar flows characteristic of microfluidics, we demonstrate the ability to generate multifunctional particles with distinct regions for analyte encoding and target capture (FIG. 1). In a typical experiment, we flowed two monomer streams (one loaded with a fluorescent dye and the other with an acrylate-modified probe) adjacently down a microfluidic channel and used a variation of continuous-flow lithography (27) to polymerize particles [with 30-ms bursts of ultraviolet (UV) light] across the streams (28). In this manner, particles with a fluorescent, graphically encoded region and a probe-loaded region can be synthesized in a single step. Each particle is an extruded two-dimensional (2D) shape (FIG. 1B) whose morphology is determined by a photomask that is inserted into the field-stop position of the microscope and whose chemistry is determined by the content of the coflowing monomer streams. The cross-linked polymer particles then flow down the channel [without sticking due to oxygen inhibition near the channel surfaces (27)], where they are collected in a reservoir. The particles can be rinsed of excess monomer and then used for biological assays.

Figure 1A:
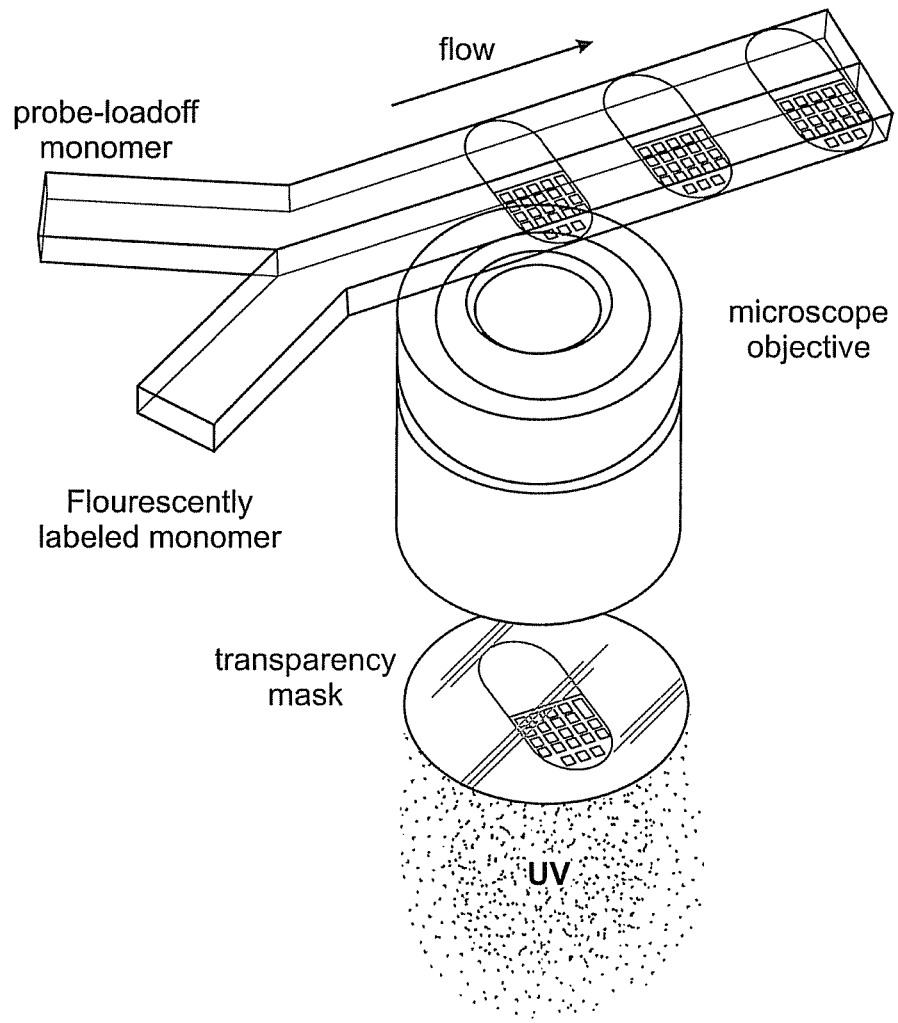
FIG. 1A is a schematic, perspective diagram of dot-coded particle synthesis showing polymerization across two adjacent laminar streams to make single-probe, half-fluorescent particles.
Figure 1B:
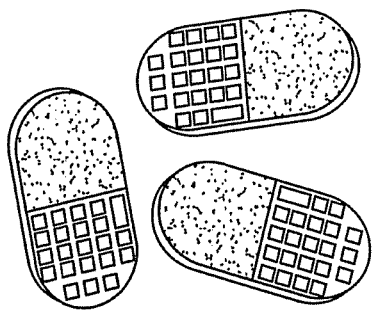
FIG. 1B is an illustration of the single-probe, half-fluorescent particles.
Figure 1C:
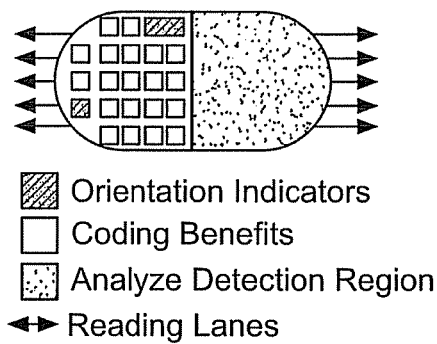
FIG. 1C is a diagrammatic representation of particle features for encoding and analyte detection.
Figure 1D:
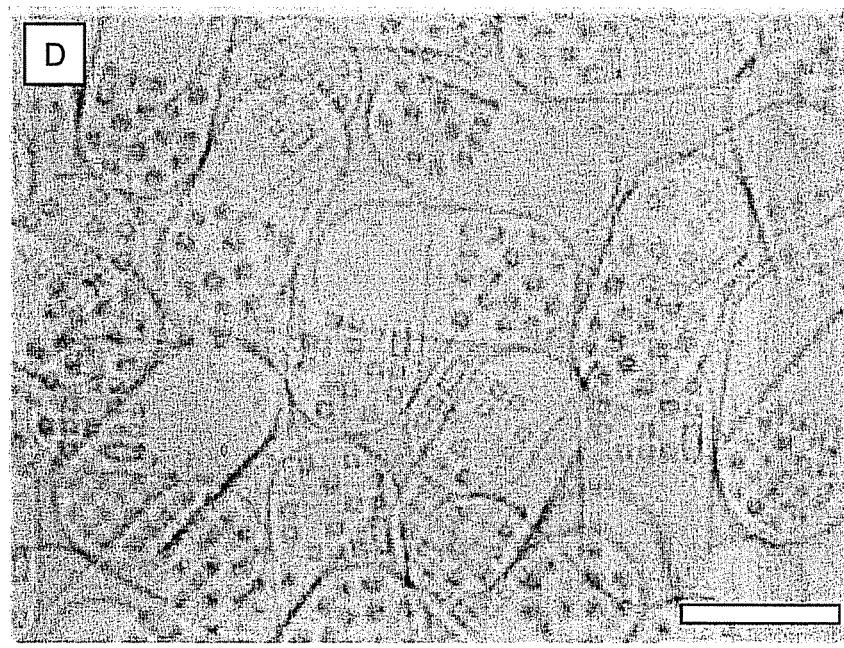
FIG. 1D is a differential interference contrast (DIC) image of particles generated by the technique shown in FIG. 1A.
Figure 1E:
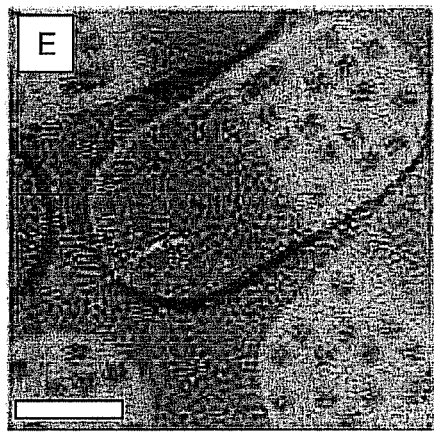
FIG. 1E is a photomicrograph of a single-probe particle.
Figure 1F:
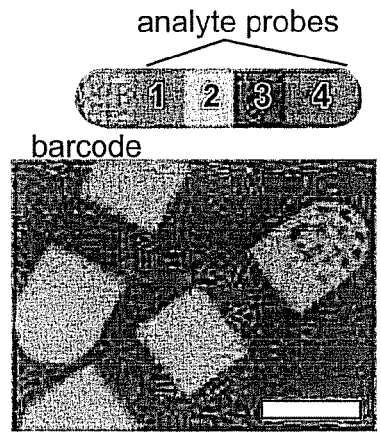
FIG. 1F is a photomicrograph showing a multi-probe particle.
Figure 1G:
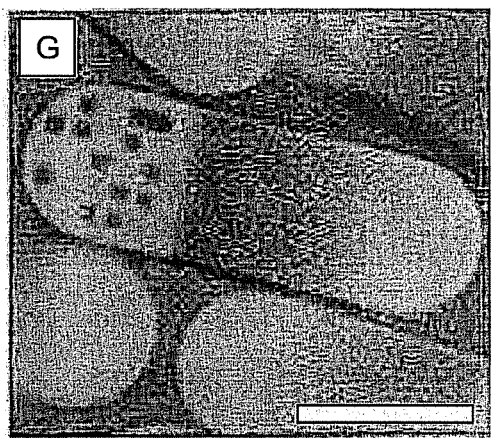
FIG. 1G is a photomicrograph showing probe-gradient encoded particles.
Figure 1H:
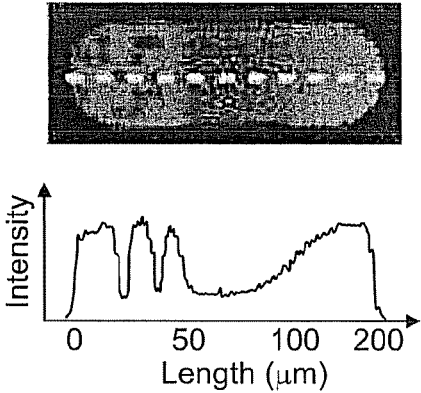
FIG. 1H is a plot of fluorescent intensity along the center line of a gradient particle.
Figure 2A:
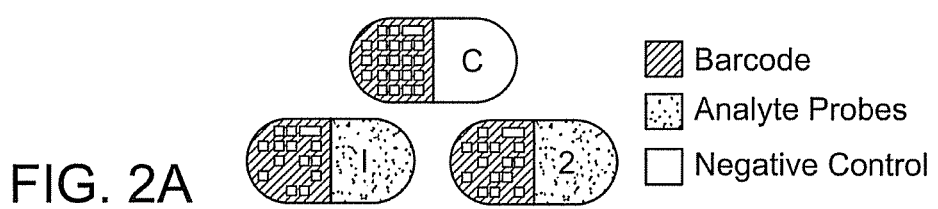
FIG. 2A-C illustrate multiplexed analysis using single-probe particles.
Figure 2B:
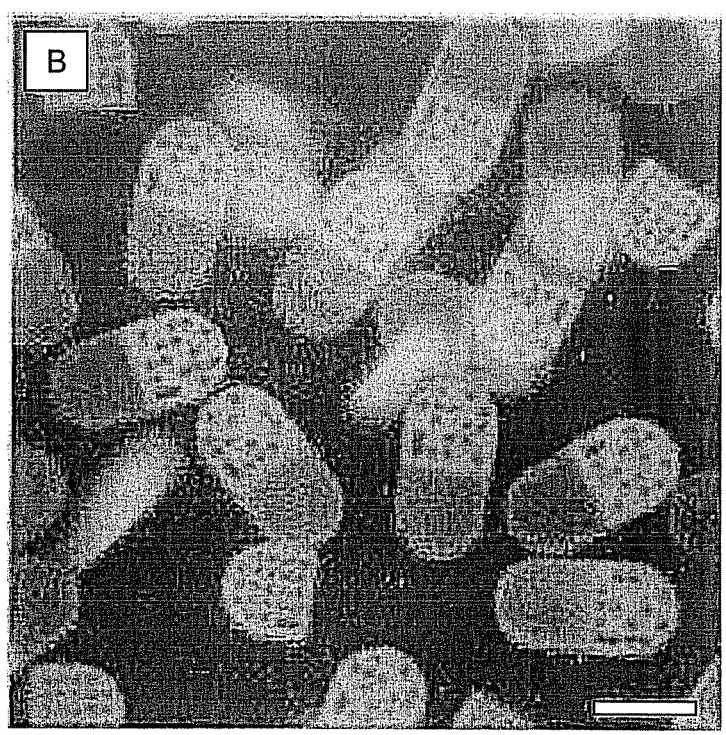
Figure 2C:
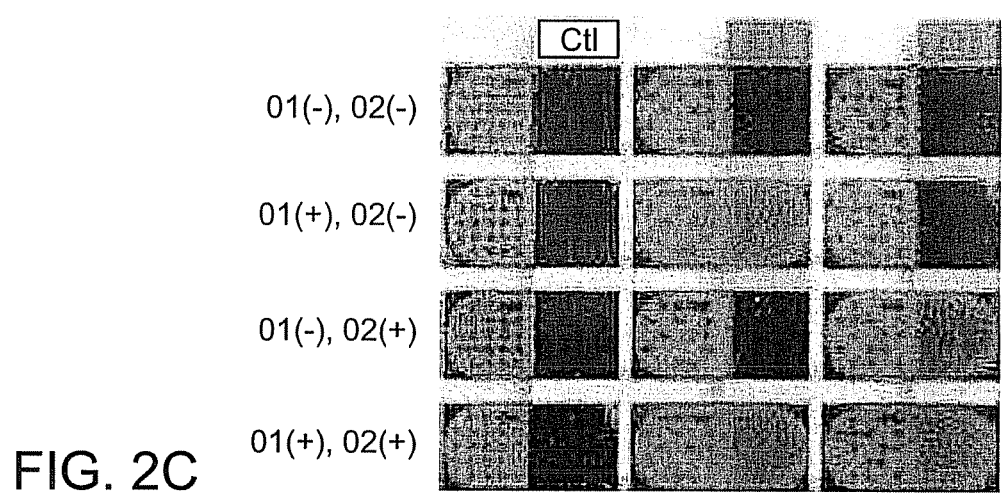
Figure 2D:
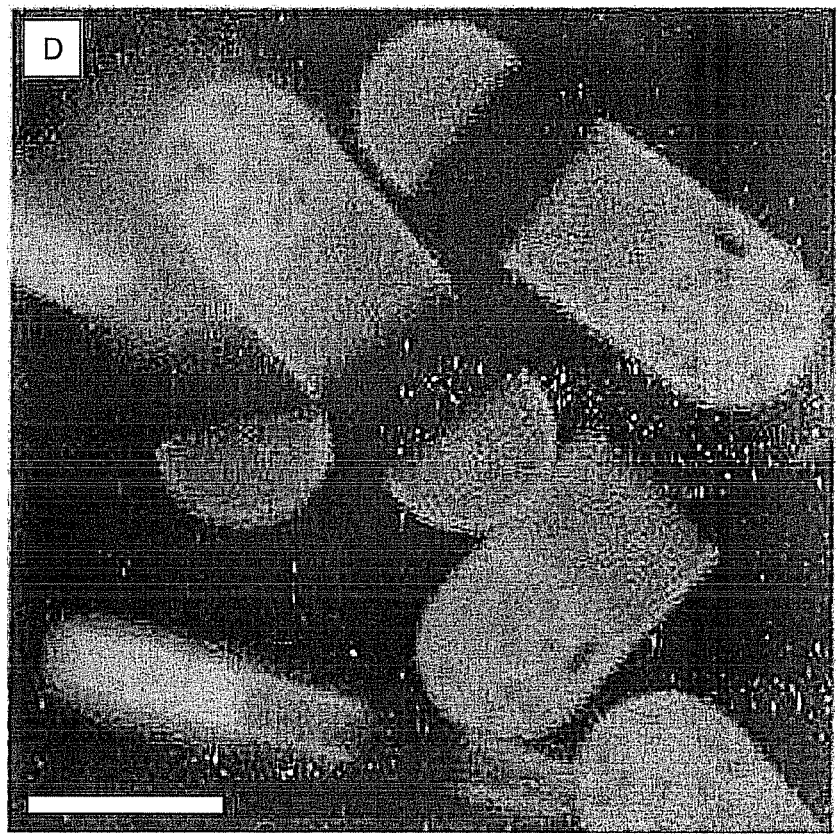
FIG. 2D-F illustrate multiplexed analysis using multi-probe encoded particles.
Figure 2E:
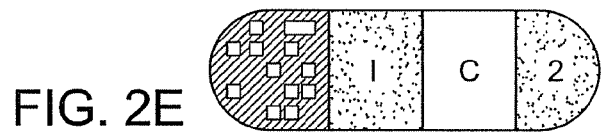
Figure 2F:
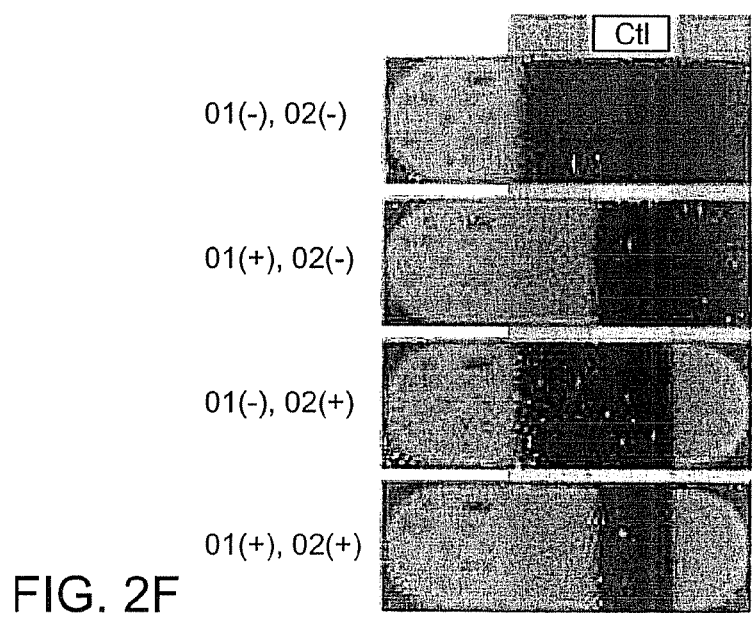

We used poly(ethylene glycol) (PEG) (well known as a bio-inert polymer) as the particle foundation to eliminate the need to "block" surfaces after probe conjugation and as a transparent material to allow transmission of fluorescent signal from both particle faces. These properties should enhance both specificity and sensitivity of analyte detection. Increasing analyte detection signal can be achieved by making the probes more accessible by increasing surface area in the probe region of the particle. Surface area can be increased by adding, for example, ridges or dimples. Signal can also be increased by increasing pore size. We used a simple dot-coding scheme to generate particles that can bear over a million ($2^{20}$) codes (FIG. 1C). Particles were designed to be "read" along five lanes down their length, with alignment indicators that were used to identify the code position and the read "direction" despite the particle orientation (FIG. 1C). The flat, long shape of the particles helps align them for scanning in a flow-through device. The spatial separation of various chemistries on the particles allows decoding and target detection to be achieved by using a single fluorophore.

To demonstrate the versatility of particle synthesis, we selectively labeled monomer streams with a fluorophore and used a variety of channel designs to generate particles bearing a single probe region, multiple probe regions, and probe-region gradients (FIG. 1, E to G). Multiprobe particles (FIG. 1F), made with the use of channels with several inlet streams, allow for a direct, single-particle comparison of several targets. Furthermore, probe gradients (FIG. 1G), made by simply allowing diffusion of the probe across streams in a long channel, are useful for broadening the detection range of an analyte when using a fixed detection sensitivity (when the signal can saturate). If magnetic nanoparticles are incorporated in a gradient, it may be possible to produce a temperature variation along particles when stimulated in an oscillating magnetic field (29).

A key feature of our method is the direct incorporation of probes into the encoded particles. This is accomplished by simply adding acrylate-modified biomolecules into the monomer solution. After polymerization, the probes are covalently coupled to the polymer network. This process is applicable for both oligonucleotide and protein probes (30-32). We demonstrate that the short bursts of UV used to synthesize probe-conjugated particles are not detrimental to the functionality of incorporated oligonucleotides. Previously, we showed similar results with bead-bound antibodies that were incorporated into polymer structures made from nearly identical monomer constituents (28, 33).

To demonstrate multiplexing capabilities, we used acrylate-modified oligonucleotide probes (which are commercially available) for DNA sequence detection (FIG. 2, A to C). We synthesized three batches of particles: one of which was loaded with 20-base pair (bp) oligonucleotide probe 1 (5'-ATA GCA GAT CAG CAG CCA GA-3') (SEQ ID NO: 1), another with probe 2 (5'-CAC TAT GCG CAG GTT CTC AT-3') (SEQ ID NO: 2), and a third with no probe, to serve as a control. Targets were fluorescently labeled oligonucleotides with complementary sequences to the two probes. We mixed the particles and incubated them for 10 min at room temperature in microwells containing either target 1 (at 1 µM), target 2 (at 1 µM), both targets (both at 0.5 µM), or no target (28). A positive target detection was indicated by probe-region fluorescence, which was more pronounced near the particle edges. This result suggested that targets were able to diffuse and hybridize several µm into the particle body (28). In each instance, the particles showed uniformity (28) with high specificity to the oligomers, exhibiting fluorescence only when the target was present (FIG. 2C).

To further demonstrate the power of our multiplexing scheme, we performed the same sequence detection assay with the use of particles with multiple adjacent functionalities (FIG. 2, D to F). In this manner, we were able to simultaneously assay for the two target sequences (with a negative control) on a single particle. Again, the assay was highly specific (FIG. 2F) and very uniform from particle to particle (FIG. 2D) (28). The interfaces between probes on the particles are very sharp, and thinner stripes could be used for even greater multiplexing capabilities.

Figure 3A:
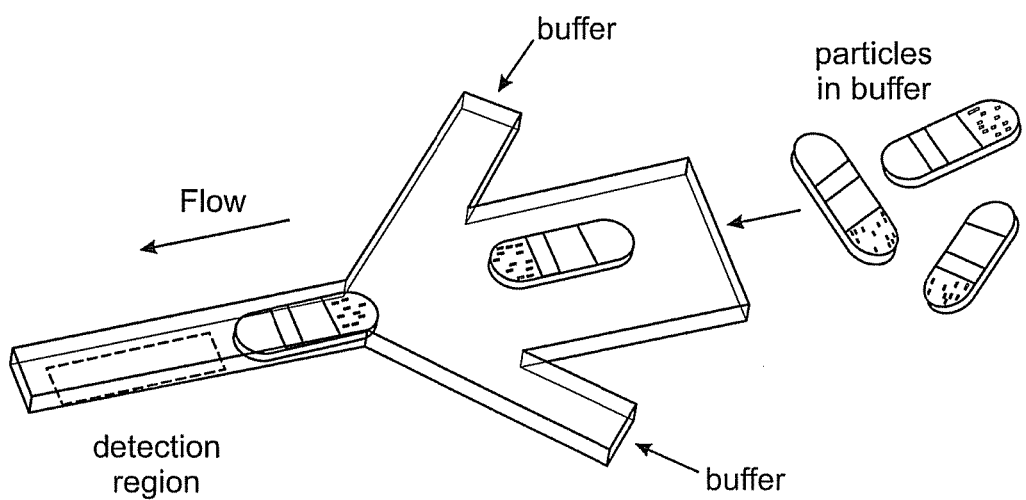
FIG. 3A is a perspective view of a schematic representation of a flow-focusing microfluidic device used to align and read particles after hybridization experiments.
Figure 3B:
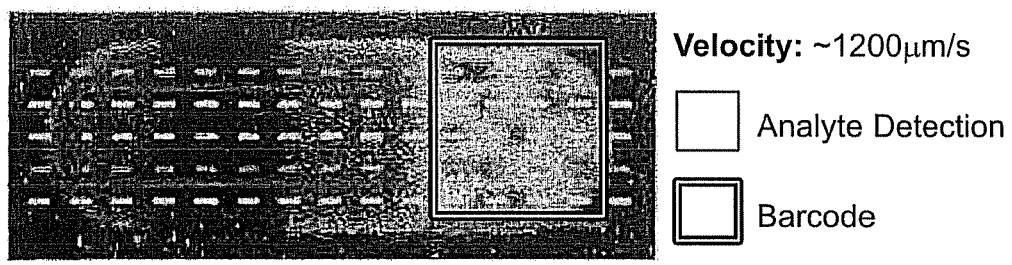
FIG. 3B is a typical image of a particle taken in a flow-through device shown in FIG. 3A.
Figure 3C:
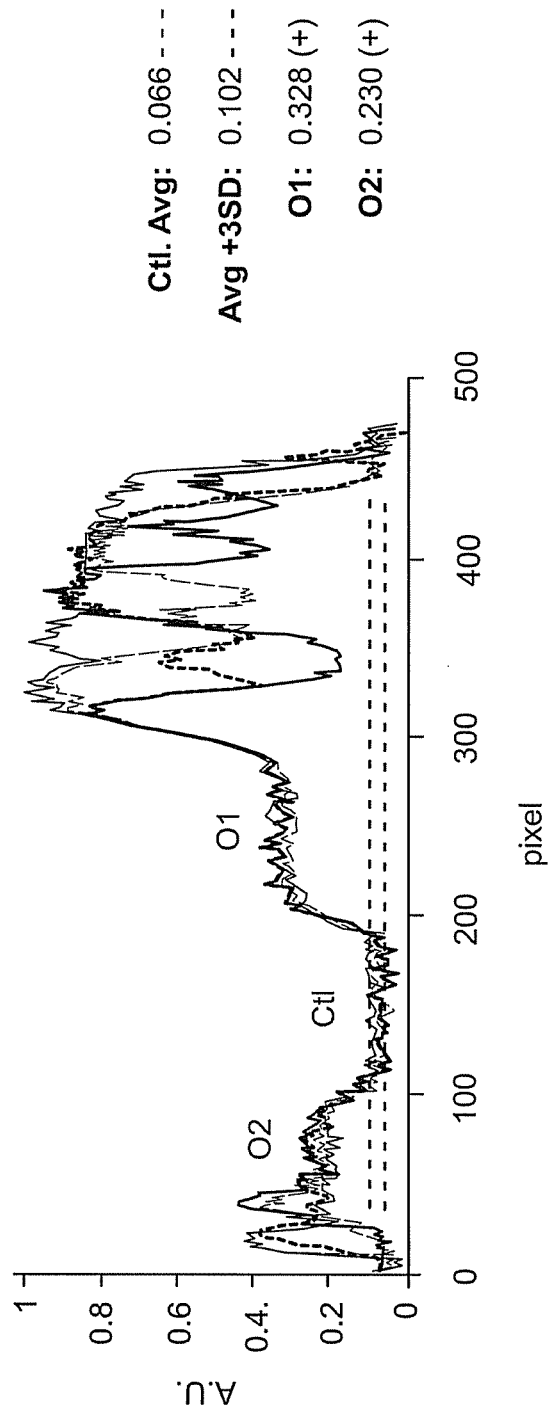
FIG. 3C is a graph showing scans of fluorescent intensity taken across the five lanes of the particle to reveal the code and to detect oligomer targets.

In order to prove that this method of multiplexed analysis is practical for high-throughput applications, we developed a simple scheme to scan particles in a flow-through device (FIG. 3). Multiprobe particles used in the hybridization experiment just described (FIG. 2, D to F) were flowed through a microfluidic channel and observed on an inverted fluorescence microscope (28). Particles were aligned by using flow-focusing and traveled down a channel only slightly larger than the particle width (FIG. 3A). We used a biofriendly surfactant (28) to ensure that the particles flowed smoothly down the channels without sticking. Images were taken at a designated detection region in the channel with an exposure of 1/125 s as the particles passed the field of view (using a 20× objective). Image sequences were later analyzed to determine the particle code and quantify targets.

A representative particle image is shown (FIG. 3B) with corresponding intensity plots along the five particle "reading lanes." The code along each lane can be determined by analyzing the sharp dips and plateaus in the intensity plots. By using the control-region fluorescence, we defined a positive target detection as the control average intensity plus three standard deviations for each particle. We were able to accurately identify the presence of both oligonucleotide targets after only a short 10-minute incubation.

Figure 4A:
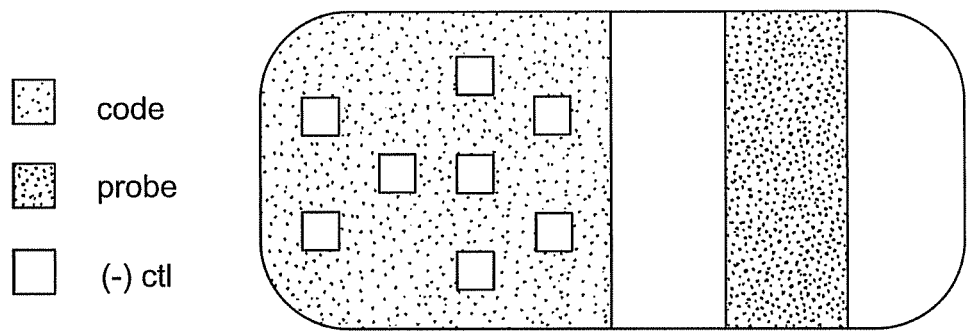
FIG. 4A is a schematic illustration of a particle including a one-dimensional encoding scheme.
Figure 4B:
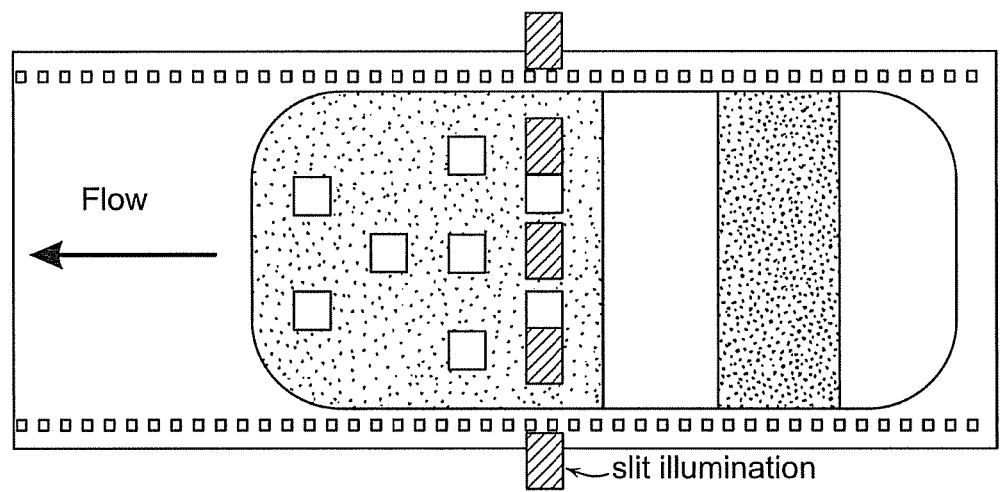
FIG. 4B is a schematic illustration showing slit illumination.
Figure 4C:
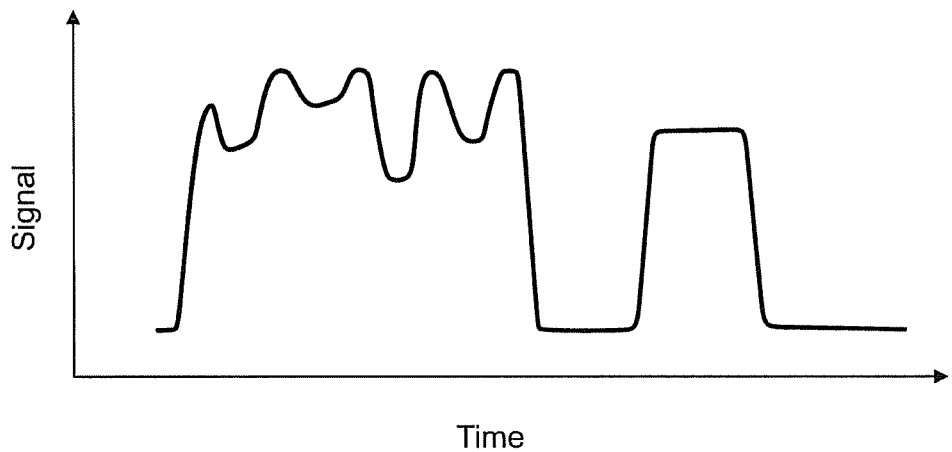
FIG. 4C is a graph of signal verses time comprising a series of valleys with varying depths in the acquired fluorescent signal.

Although the two-dimensional dot-pattern scheme discussed above is extremely powerful, it will require fairly sophisticated spatial detection. A potentially more practical, "one-dimensional" encoding scheme shown in FIG. 4 is capable of providing a more modest approximately 2,500 codes. As with the two-dimensional arrangement, the code will be a series of holes in a fluorescent background, but will be one-dimensional in that they provide a series of peaks and valleys when scanned across the entire width as shown in FIG. 4C. The embodiment in FIG. 4 is reproducable (preferably with a built-in "calibration") so as to ensure decoding accuracy and will not significantly affect particle integrity or required size.

In order to accurately and rapidly scan particles in this embodiment, we will use a detection scheme that provides rapid sampling with extremely sensitive light detection. Traditional microarray scanners and flow cytometers (and their microfluidic counterparts) utilize photomultiplier tube (PMT) modules for this purpose (37, 42, 43). These systems provide an extremely high sampling rate (~MHz) and extraordinary sensitivity, which makes them ideal for this application. These modules can be mounted directly to the camera port of a microscope and used seamlessly with the flow-focusing devices discussed above, given the appropriate illumination source and used with standard data acquisition software.

In a simple setup of this embodiment of the invention, the PMT module will collect all of the light relayed through the microscope port. Therefore, to obtain spatial information that will be used to decode the particles, it is preferred to illuminate only a thin-slit region perpendicular to the direction of particle movement. The slit size will be set by the encoding and probe feature sizes, which will likely be on the order of 10 µm. This resolution can be achieved by simply using a mask with our projection photolithography setup (27). More sophisticated illumination sources such as line-focused laser beams can also be used (44, 45). In another embodiment of the invention, broad illumination can be used with a slit-like filter placed in front of the PMT detector.

The throughput of our system is primarily determined by the detection scheme and the particle size. The particles synthesized for this study are relatively large compared with those in other flow-through methods, measuring 90 µm in width, about 30 µm in thickness, and 180 to 270 µm in length. In some embodiments, for this study, we synthesized particles that were 90 µm wide, ~30 µm thick and 180, 270, or 450 µm long. Large size not only limits the throughput of a system but also increases the sample volume. However, the great particle-to-particle reproducibility we have demonstrated (28) will afford a much lower redundancy than is typical in flow-through systems, improving efficiency. By using conservative estimates, we found that our system should be capable of providing rapid, high-density analysis with a manageable sample volume (28) despite the seemingly large particle size.

In addition to being very reproducible, we have also shown that our system is very sensitive. With 30-min incubations, we can detect DNA oligomers comfortably at 500 attomoles without biotin-avidin-aided signal amplification (28). This leads us to believe that our system will be at least as sensitive as current, commercially available multiplexing technologies, with the added advantages of all-in-one particle synthesis, incorporation of multiple probes, low cost (28), virtually unlimited codes, and implementation using little more than a standard fluorescence microscope.

EXAMPLES

Materials and Methods

Materials

Particles synthesized in this work were made from monomer solutions based on poly(ethylene glycol)diacrylate (PEG-DA, Aldrich, $M_n$=700) with 2-hydroxy-2-methylpropiophenone photoinitiator (Aldrich). For hybridization experiments, we used monomer solutions of 2:1 PEG-DA:TE Buffer (10 mM Tris pH 8.0 (Rockland), 1 mM EDTA (OmniPur)) with 1-2.5% initiator and a DNA oligomer probe at a concentration of 50 µM. Oligomer probes (IDT) came modified with a reactive Acrydite group and 18-carbon spacer (Probe #1: 5'-Acrydite-C18-ATA GCA GAT CAG CAG CCA GA-3' (SEQ ID NO: 1), Probe #2: 5'-Acrydite-C18-CAC TAT GCG CAG GTT CTC AT-3' (SEQ ID NO: 2)). Encoded-region fluorescence was obtained by incorporating 0.005 wt % of methacryloxyethyl thiocarbamoyl rhodamine B (Polysciences) in the respective monomer solution with 1% blue food coloring to easily visualize the co-flowing streams using bright-field microscopy.

Microfluidic Devices

Microchannels were generated using standard procedures in soft lithography. Polydimethylsiloxane (PDMS) elastomer (Sylgard 184, Dow Corning) was cured on a silicon wafer bearing channel reliefs made using SU-8 photoresist (Microchem). Channels were designed such that multiple (2-7) 100 µm-wide inlet channels converged into a common, wider channel (200-500 µm wide). The channels (and reservoirs) were cut out with a scalpel, a hole was punched at each inlet, and the channels were sealed to PDMS-coated glass slides. Pipette tips (10 µl, Molecular BioProducts), connected with rubber tubing (Tygon) to a common pressure source (regulated by a pressure valve, Controlair Inc.), were each filled with ~5 µl of polymer and inserted into the channel inlet ports. A three way solenoid valve (Burkert, operated manually) allowed for the oscillation between pressurized (~1 psi, high velocity) and ambient-pressure (no flow) states.

Photopolymerization Setup

Photomasks designed using AUTOCAD were printed with 20 000 dpi resolution at CAD/Art Services, Inc. (Brandon, Oreg.). The masks were inserted into the field-stop position of a Zeiss Axiovert 200 microscope, equipped with a 100 W HBO mercury lamp and wide-excitation ultraviolet (UV) filter set (11000v2:UV, Chroma). A computer-driven shutter system (UniBlitz) was in place to provide the desired pulses of UV excitation. Particles were polymerized across adjacent streams in a microfluidic channel with 30-50 ms bursts of UV excitation. Using the three way valve to control flowrate, particles were polymerized in a no-flow state and immediately flushed down the channel in a pressurized state—providing clean interfaces between adjacent streams with high resolution of particle features. Visual alignment for polymerization was achieved using a CCD camera (KPM 1A, Hitachi) with NIH Image software.

Particle Recovery

Particles were collected in a reservoir after polymerization where they were cleaned of unreacted monomer. The particles were rinsed several times with TE buffer, then with PEG-DA monomer, and again with TE buffer until all residual fluorescence was gone. After each rinse, the particles were allowed to settle to the bottom of the reservoir and excess rinsing solution was pipetted from the top. Particles were typically used immediately for hybridization experiments but were occasionally used after being stored for several days in a dark environment, showing no loss of functionality.

Oligomer Hybridization

Particles were pipetted into separate PDMS reservoirs for each hybridization experiment. Complementary target DNA oligomers modified with a Cy3 fluorophore (IDT) were suspended at concentration of 1 μM in hybridization buffer (TE buffer with 0.2M NaCl (Mallinckrodt) and 0.5% sodium dodecyl sulfate (SDS, Invitrogen)). Solutions of target oligomer were pipetted into the appropriate reservoirs and the particles were incubated for 10 min at room temperature. The particles were then rinsed several times with TE buffer and visualized using an orange longpass filter set (XF101-2, Omega), which is compatible with both rhodamine B and Cy3 fluorophores. Still images were captured using a Nikon D200 digital camera.

Particle Reading

Flow-focusing microfluidic channels were plasma-sealed at the inlets on a PDMS-coated glass slide. Prior to particle reading, the channel was flushed with "read buffer" (TE with 25% PEG-DA and 0.5% Tween 20) for 5 min. Multi-probe particles used in hybridization experiments were resuspended in read buffer and pipetted into the channel reservoir. The pressure system described previously was used with a column of water to pull a vacuum on the channel and induce fluid flow. Particles were observed flowing through a 100 μm channel constriction with a Zeiss Axiovert 200 microscope and imaged with an exposure of 1/250 sec under fluorescence with a CCD camera (Hitachi KPM1A). Movies were taken using NIH image at 10 frames per second—particle velocities were calculated and intensity profiles were taken along the 5 "lanes" of each particle. The average and standard deviation of the intensity along the control region of a particle were taken. A positive reading for an oligomer target was defined as the average plus three standard deviations of the negative control signal.

Investigation of Particle Composition

Probe Concentration

Figure 5:
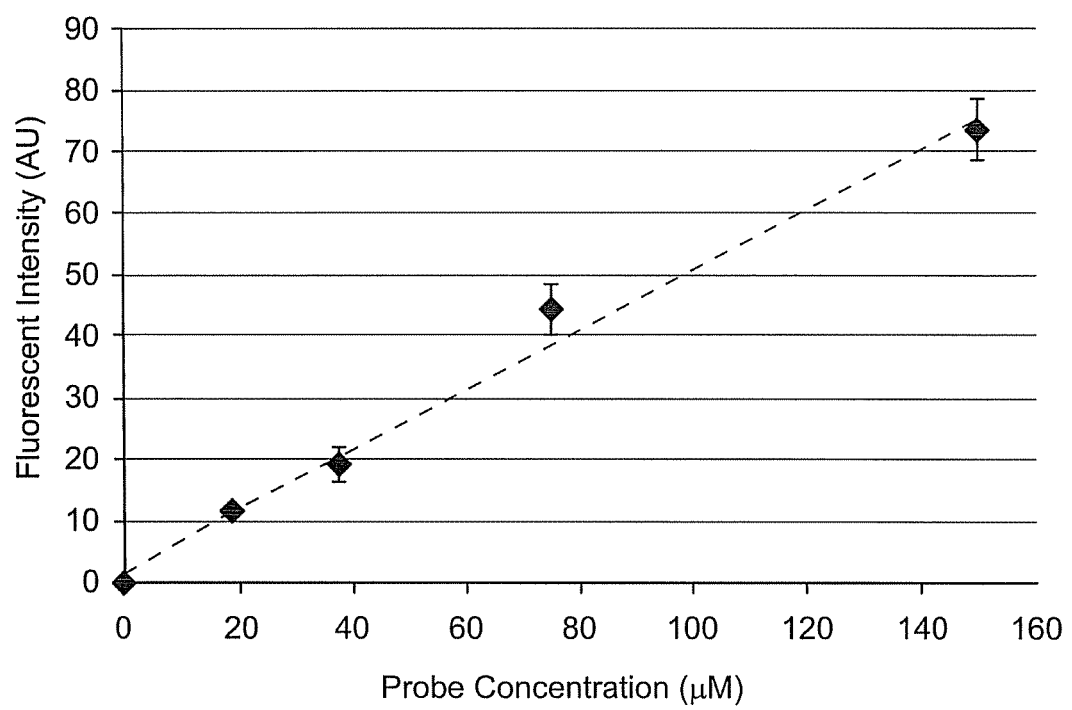
FIG. 5 is a graph showing fluorescent intensity of particles with varying probe concentrations.

We used serial dilution of an oligomer probe in monomer to determine the effect of concentration on signal detection. We synthesized particles with probe concentrations of 150, 75, 37.5, and 18.75 μM. Control particles (0 μM probe) were used to determine the background intensity ($I_b$). The particles were incubated for 30 min with a fluorescent-labelled target at 1 rinsed, and imaged to determine fluorescent intensity ($I_p$). The fluorescent signal is reported in arbitrary units (AUs) taken as the difference $I_p-I_b$. The results are shown in FIG. 5. The error bars on the graph represent the standard deviation in each measurement, with an average coefficient of variation (COV) of 9%.

As can be seen, the intensity increases linearly with probe concentration. This finding is expected when considering the binding of two complementary oligomers—at equilibrium, the relationship is given as:

$$T+P \rightleftharpoons TP$$

where T=target, P=probe, and T P=double stranded complex. At equilibrium, the concentrations of the species can be characterized by a dissociation constant, $K_d$, such that:

$$K_d = \frac{[P][T]}{[PT]}$$

If $[T]_o \gg [P]_o$ as is the case in our experiment, then $[T] \approx [T]_o$. Using this, and the relationship $[P]=[P]_o-[PT]$, we obtain:

$$[PT] = \frac{[P]_o[T]_o}{K_d + [T]_o}$$

Thus, for a given initial concentration of target, we can expect the signal (which is proportional to [PT]) to be linear with respect to the probe concentration. Although we could obtain a much higher signal with increased probe concentration, we chose to incorporate 50 μM probe for proof of principle experiments—this concentration gave sufficient signal for target detection with minimal usage of oligomer.

Monomers

We investigated the use of several polymers for barcoded particles, including poly(ethylene glycol)diacrylate of three chain lengths ($M_n$=200, 400, 700) and also a blend of acrylamide with PEG-DA as crosslinker. The characteristics investigated when selecting a polymer blend were (1) fast polymerization kinetics, (2) low background fluorescence before hybridization, and (3) a strong fluorescence signal after hybridization. All solutions we made consisted of monomer (pure or at 2:1 with TE buffer), 2.5% photoinitiator, and DNA oligomer at 50 μM. Particles were made using 30 ms UV exposure with a 20× objective.

We found that hybridization signals were significantly higher when TE buffer was included in the monomer blend. This is consistent with our previous work (33), in which we discovered that bead-bound proteins incorporated in polymerized PEG hydrogels lost functionality in the absence of buffer. We found that PEG-DA ($M_n$=700) had significantly faster reaction kinetics than the other monomers and also showed significantly less background signal. The final monomer solution we chose for hybridization experiments was a 2:1 blend of PEG-DA:TE with 1-2.5% photoinitiator.

Particle Characterization

Polydispersity

It is very important that the particles being used for quantitative biomolecule analysis be consistent both morphologically and functionally. We have already shown that particles synthesized using continuous-flow lithography have a very low coefficient of variation (<2%) with respect to physical size (27). We also performed experiments to investigate the variation of fluorescent signal for particles used in a hybridization study.

The fluorescent intensity of particles used in a hybridization study gives evidence of the "functional" polydispersity of the particles. However, this measure is not only dependent on the particles, but also on the hybridization experiment itself—the numbers we present should be a conservative estimate. We found the COV of fluorescent signal to range from 6-10% when incubating with target at concentrations of 1 µM-10 nM and increase to ~15-30% for lower concentrations (down to 10 pM).

Active Probe Concentration

Figure 6:
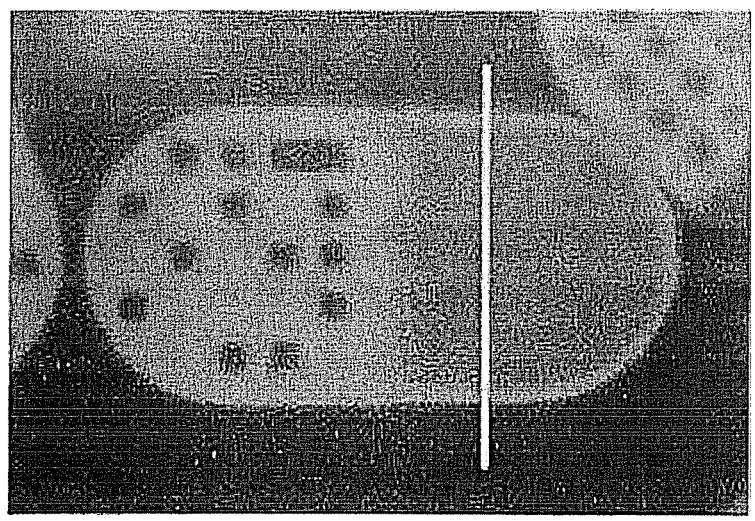
FIG. 6 is a plot of fluorescent intensity across a particle section after target hybridization. The white line on the particle image indicates the region that was scanned.
Figure 6:
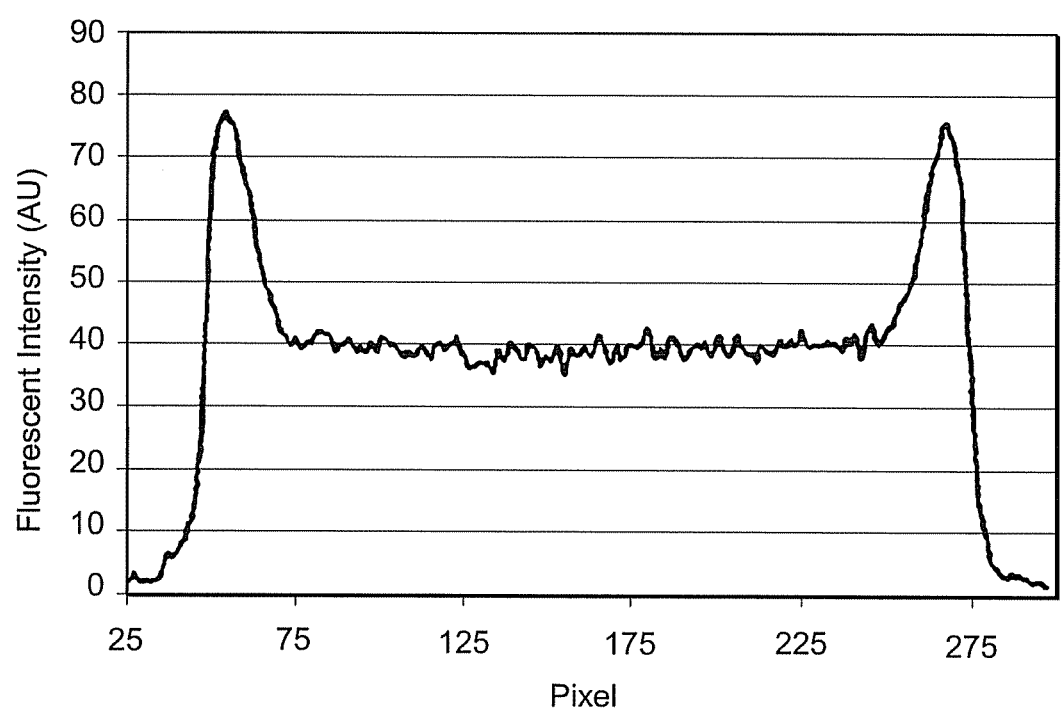

In order to calculate the concentration of probe on the particle surfaces, we used the concentration of probe incorporated into our monomer solution (50 µM) with an estimate of the depth to which oligomers can diffuse into particles and react. Shown in FIG. 6 is a typical particle used in a hybridization study with a scan of fluorescent intensity across its sensing region.

As can be seen, the particle shows a significantly higher signal at the edges of its sensing region—the coded region does not show this characteristic because the fluorescent dye incorporated has been homogeneously distributed throughout. We assumed that this "edge" signal was proportional to the amount of oligomer bound to the 30 µm-thick edge of the particle. The intensity in the interior of the particle was almost exactly ½ that of the edge for the several particles we investigated. Assuming that all surfaces are similar, we deduced that the active binding thickness in the interior of the particle must be $$30\ \mu m \times \frac{80.417}{40.417} = 15\ \mu m,$$

or ~7.5 µm per face. As validation, we can see that the width of the high-intensity region at each particle edge is ~20 pixels=8 µm. Physically, this can be explained by the pore size. The polymerization of particles occurs most rapidly at the center (where oxygen must diffuse the furthest and the concentration of free radicals is the highest) and slower at the particle surface. Therefore, we can assume that the particles are more tightly crosslinked at the center than near the surfaces, providing larger pores into which short oligomers can diffuse and react with complementary probes. Based on the work of others, the PEG polymer we used should have a pore size of ~10 Å when completely crosslinked (34, 35).

Using the probe concentration of 50 µM (in monomer), with an active thickness of 7.5 µm per face and a 50% incorporation efficiency, we estimated the effective surface concentration to be:

$$\frac{50\ \mu M}{7.5\ \mu m} \times 50\% \simeq 1 \times 10^5 \frac{\text{molecules}}{\mu m^2}\ \text{per face}$$

Because the particles are transparent, the fluorescence of both faces should give a projected probe concentration of $$2 \times 10^5 \frac{\text{molecules}}{\mu m^2}, .$$

This is a similar "surface" concentration to those reported by others (36). As mentioned previously, we can incorporate a substantially greater amount of probe into our particles to make the surface concentration much higher, thus increasing the sensitivity of our system.

Estimation of Throughput

Recently, microfluidic-based flow cytometers have been developed with integrated photomultiplier tubes to achieve a very high throughput. The fluid velocities in these systems can be on the order of 10 m/s (similar to conventional flow cytometers) while detection is carried out at a high sample rate of 5 MHz, allowing a particle read rate of 17,000/sec (37). We use this as a basis to estimate the throughput we can achieve with our system when incorporating more sophisticated sensing schemes. Conservatively, we estimated a flow velocity of 1 m/s and a spacing of 10 particle lengths between particles (each 200 µm in length). Thus, we can calculate a throughput of $$\text{THROUGHPUT} = 1 \frac{\text{meter}}{\text{sec}} \times \frac{1}{2,200} \frac{\text{particle}}{\mu m} \approx 450 \frac{\text{particles}}{\text{sec}}.$$

Although this "particle/sec" throughput seems lower than that typically seen in flow cytometry, we discuss why on a "target/sec" basis, the technology should provide a sufficient throughput for high-density analysis.

We have shown that our system exhibits excellent particle-to-particle reproducibility (as discussed above). Enzyme-linked immunosorbant assays (ELISAs), which are considered to be the gold standard in sensing, show similar precision (38) to our technology and are typically done only in duplicate. This level of redundancy is significantly lower than seen in flow cytometry-based assays. We will assume for estimation purposes that our assays can be performed in triplicate to yield accurate information. With a redundancy of 3, our "target/sec" throughput becomes $$\text{THROUGHPUT} = 450 \frac{\text{particles}}{\text{sec}} \times \frac{1}{3} \frac{\text{target}}{\text{particles}} \approx 150 \frac{\text{targets}}{\text{sec}}.$$

Two simple modifications that will provide an even higher throughput are (1) reduction of particle size, and (2) incorporation of several probes on a single particle. We have demonstrated in our lab the ability to produce particles with features on the order of ~1 µm, so it is well within reason to consider the production of encoded particles that are half-sized in each dimension. This would increase the number of particles/volume by a factor of 8. Furthermore, if the particles have 3 functionalities (two probes and a control as in FIG. 6), this increases the throughput by another factor of 2. Using these arguments, we can calculate some expected throughputs:

TABLE 1

Estimation of throughput and particle volume for tests done in triplicate (each probe appears on three particles).

| Particle Size | Probes/Particle | Throughput $\left(\frac{\text{targets}}{\text{sec}}\right)$ | Particle Volume $\left(\frac{\mu L}{10^6\ \text{targets}}\right)$ |
|---|---|---|---|
| Normal | 1 | 150 | 1,800 |
| Half | 1 | 300 | 225 |
| Normal | 2 | 300 | 900 |
| Half | 2 | 600 | 113 |

"Normal" particle size is ~100 × 200 × 30 µm, while "half" size is ~50 × 100 × 15 µm. Particle volume is based on $10^6$ targets tested, which for single and two-probe particles corresponds to $3 \times 10^6$ and $1.67 \times 10^6$ total particles, respectively.

From this simple analysis, it seems reasonable to analyze one million targets in less than one hour when using reduced-size and/or multi-probe particles. This analysis also highlights the importance of particle size in terms of volume—reduced-size particles will likely be necessary for high-density analysis.

Limits of Detection

Figure 7:
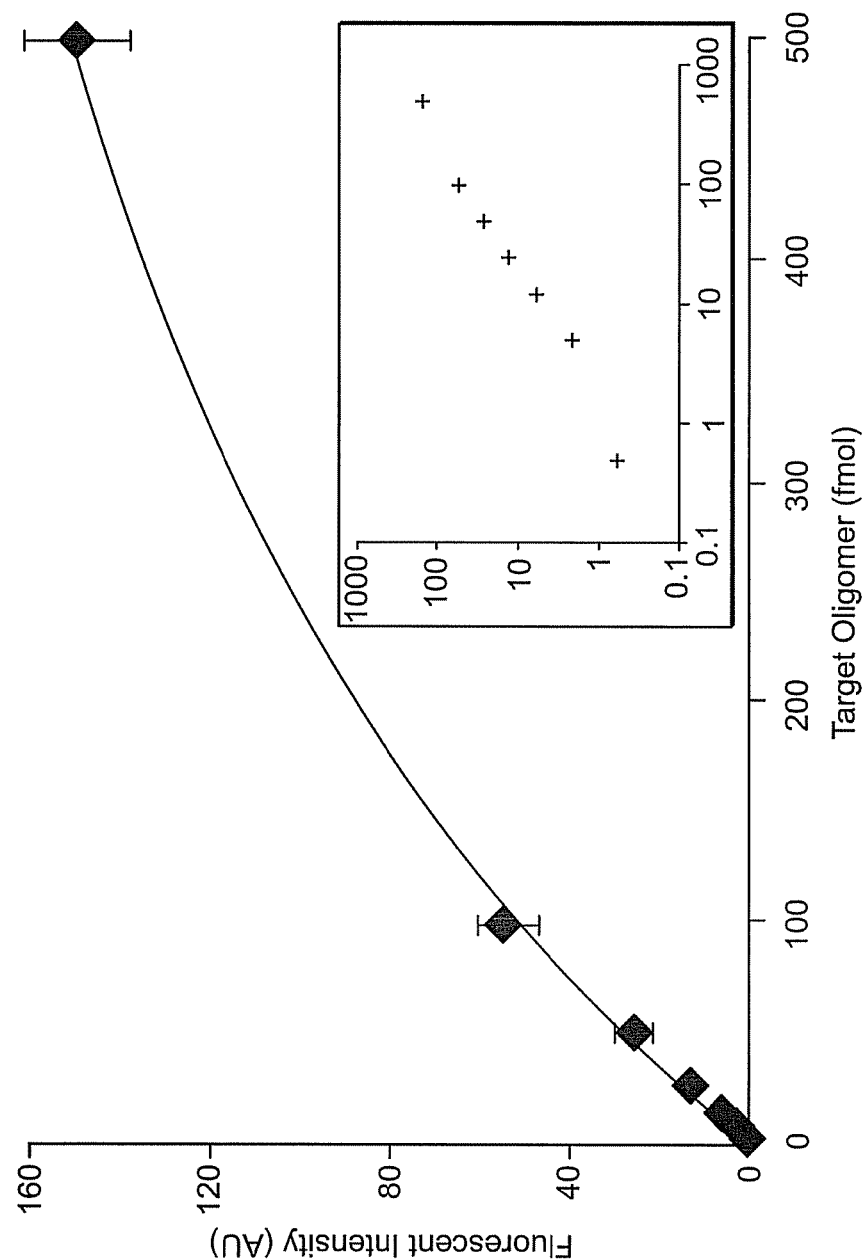
FIG. 7 is a plot of hybridization signal (fluorescent intensity) of particles incubated at varying target concentrations.

We hybridized particles with fluorescent target at concentrations spanning over several orders of magnitude in order to determine a suitable range of detection. Samples of particles from a common batch (with 50 µM probe incorporated) were incubated with 50 µl of target solution for 30 min at room temperature on a vortex mixer—target concentrations ranged from 10 nM-10 pM corresponding to 500 fmol-500 amol ($10^{-18}$ moles) of oligomer. After hybridization, the particles were rinsed and imaged under fluorescence for detection with an EB-CCD camera (C7-190-20, Hamamatsu) mounted to our microscope. Because the system had an 8-bit limited dynamic range, it was necessary to use three different sensitivity settings to accommodate the broad range in fluorescent signal. As such, two of the particle batches were imaged at two of the three sensitivity settings so the signals could be normalized and plotted on a common scale. The results of the detection study are shown in FIG. 7.

As can be seen, this plot is not linear as was the case with varying probe concentrations (FIG. 5). This is because at lower target concentrations, the amount of target is no longer much greater than the amount of probe ($[T]_o \gg [P]_o$), and the approximation that $[T]=[T]_o$ can no longer be made. Additionally, it is known that the time taken to reach equilibrium increases with decreasing target (39)—the incubation time used in this experiment (30 min) was not likely sufficient for this to occur.

We found the assay to be quite sensitive, detecting oligomer comfortably at the lowest amount tested (500 amole) without biotin/avidin-based signal amplification. This finding suggests that our system has a comparable sensitivity to the current state of the art multiplexing systems including Affymetrix (40) and Luminex (41). Furthermore, we showed previously that we can increase the sensitivity of the assay by incorporating higher probe concentrations of probe into the particles.

Cost of Materials

At standard non-bulk pricing, the raw material cost to produce 1 million single-probe particles similar to those presented in the manuscript is only $ 4.28 ($ 0.14 without DNA probe) as outlined below:

TABLE 2

Estimation of raw material cost to produce $10^6$ particles (~100 × 200 × 300 µm) with DNA oligomer probe incorporated at a concentration of 50 µM.

| Component | Unit Price | Price per $10^6$ Particles |
|---|---|---|
| PEG Monomer | $50/500 ml | $0.06 |
| Photoinitiator | $80/250 ml | <$0.01 |
| Fluorescent Dye | $560/1 g | $0.08 |
| 20 bp DNA Probe | & 276/1 µmole | $4.14 |
| | | Total: $4.28 |

As described earlier, it would be reasonable to make particles half-sized in each dimension, which would reduce particle volume and cost by a factor of 8 (to only $ 0.54 per $10^6$ particles). It is also important to note that very little sample is wasted due to the low-volume microfluidic processing.

The microchannels used for particle synthesis and flow-through reading are of simple design and can be generated very economically. A single 4" wafer (<$100), generated using standard SU-8 lithography, can easily bear over 10 channels and be molded from many times (we assume 10 times for subsequent calculations). In addition, each device may be used several times (we will use 5). Therefore, using very conservative estimates, the device cost would be:

TABLE 3

Estimated cost of microdevices used for particle synthesis and flow-through reading.

| Component | Unit Price | Price per Device |
|---|---|---|
| Fabrication of Master | $100/100 channels | $1.00 |
| PDMS | $0.10/g | $0.25 |
| Microscope Slide | $100/400 | $0.25 |
| | | Total: $1.50 |
| | | Price per use: $0.30 |

It was assumed that master wafers have 10 channels and can be molded 10 times, and that each device could be used 5 times before being discarded.

The material cost for a single multiplex experiment with a million particles would be <$5.00 ($4.28 for the particles and $0.60 for one "synthesis" and one "read" channel). This estimate does not include the buffer used in particle reading, which consists of inexpensive materials and would be negligible in the overall cost.

REFERENCES

1. D. Gershon, *Nature* 416, 885 (2002).
2. S. P. Fodor et al., *Nature* 364, 555 (1993).
3. G. MacBeath, S. L Schreiber, *Science* 289, 1760 (2000).
4. R. J. Fulton, R. L. McDade, P. L. Smith, L. J. Kienker, J. R. Kettman Jr., *Clin. Chem.* 43, 1749 (1997).
5. B. J. Battersby et al., *J. Am. Chem. Soc.* 122, 2138 (2000).
6. H. Xu et al., *Nucleic Acids Res.* 31, e43 (2003).
7. M. Han, X. Gao, J. Z. Su, S, Nie, *Nat. Biotechnol.* 19, 631 (2001).
8. X. W. Zhao et al., *Chem. Mater.* 18, 2443 (2006).
9. F. Cunin et al., *Nat. Mater.* 1, 39 (2002).
10. X. Su et al., *Nano Lett.* 5, 49 (2005).
11. H. Fenniri, S. Chun, L. Ding, Y. Zyrianov, K. Hallenga, *J. Am. Chem. Soc.* 125, 10546 (2003).
12. S. R. Nicewarner-Peña et al., *Science* 294, 137 (2001).
13. M. Y. Sha et al., *Anal. Bioanal. Chem.* 384, 658 (2006).
14. M. Evans, C. Sewter, E. Hill, *Assay Drug Dev. Technol.* 1, 199 (2003).
15. Z. L. Zhi, Y. Morita, Q. Hasan, E. Tamiya, *Anal. Chem.* 75, 4125 (2003).
16. K. Braeckmans et al., *Nat. Mater.* 2, 169 (2003).
17. E. J. Moran et al., *J. Am. Chem. Soc.* 117, 10787 (1995).
18. K. C. Nicolaou, X. Y. Xiao, Z. Parandoosh, A. Senyei, M. P. Nova, *Angew. Chem. Int. Ed.* 34, 2289 (1995).
19. R. F. Service, *Science* 270, 577 (1995).
20. T. M. McHugh, R. C. Miner, L H. Logan, D. P. Stites, *J. Clin. Microbial.* 26, 1957 (1988).
21. A. R. Vaino, K. D. Janda, *Proc. Natl. Acad. Sc. U.S.A.* 97, 7692 (2000).
22. J. P. Nolan, L. A. Sklar, *Trends Biotechnol.* 20, 9 (2002).
23. J. B. Fan, M. S. Chee, K. L Gunderson, *Nat. Rev. Genet.* 7, 632 (2006).
24. J. A. Ferguson, F. J. Steemers, D. R. Walt, *Anal. Chem.* 72, 5618 (2000).
25. N. H. Finkel, X. Lou, C. Wang, L. He, *Anal. Chem.* 76, 352A (2004).

26. K. Braeckmans, S. C. D: Smedt, M. Leblans, R. Pauwels, J. Demeester, *Nat. Rev. Drug Discov.* 1, 447 (2002).
27. D. Dendukuri, D. C. Pregibon, J. Collins, T. A. Hatton, P. S. Doyle, *Nat. Mater.* 5, 365 (2006).
28. Materials and methods are available as supporting material on *Science* Online.
29. R. Hergt et al., *IEEE Trans. Magn.* 34, 3745 (1998).
30. A. Y. Rubina et al., *Biotechniques* 34, 1008 (2003).
31. A. V. Vasiliskov et al., *Biotechniques* 27, 592 (1999).
32. F. N. Rehman et al., *Nucleic Acids Res.* 27, 649 (1999).
33. D. C. Pregibon, M. Toner, P. S. Doyle, *Langmuir* 22, 5122 (2006).
34. M. B. Mellott, K. Searcy, M. V. Pishko, *Biomaterials* 22, 929 (2001).
35. G. M. Cruise, D. S. Scharp, J. A. Hubbell, *Biomaterials* 19, 1287 (1998).
36. Y. Kohara, H. Noda, K. Okano, H. Kambara, *Nucleic Acids Res.* 30, e87 (2002).
37. C. Simonnet, A. Groisman, *Anal. Chem.* 78, 5653 (2006).
38. W. de Jager, G. T. Rijkers, *Methods* 38, 294 (2006).
39. P. W. Stevens, M. R. Henry, D. M. Kelso, *Nucleic Acids Res.* 27, 1719 (1999).
40. R. A. Irizarry, Z. Wu, H. A. Jaffee, *Bioinformatics* 22, 789 (2006).
41. S. A. Dunbar, C. A. V. Zee, K. G. Oliver, K. L. Karem, J. W. Jacobson, *J. Microbiol. Methods* 53, 245 (2003).
42. Wang et al., *Lab Chip*, 4, 2004.
43. McClain et al., *Anal. Chem.,* 73, 2001.
44. Eyal and Quake, *Electrophoresis,* 23, 2003.
45. Sinclair et al., *App. Optics,* 43, 2004.

the particle and further wherein the particle is greater than about 100 μm up to about 450 μm in at least one dimension.

2. The polymeric particle of claim 1, wherein the probe includes an inert species to serve as a negative control.

3. The polymeric particle of claim 1, wherein the encoded region comprises spatially patterned features selected from a plurality of open and closed coding elements.

4. The polymeric particle of claim 3, wherein the coding elements are arranged in a two-dimensional grid.

5. The polymeric particle of claim 4, wherein the grid includes 20 coding elements.

6. The polymeric particle of claim 1, wherein the polymeric particle further comprises at least one orientation indicator.

7. The polymeric particle of claim 3, wherein the coding elements have non-uniform shapes or sizes.

8. The polymeric particle of claim 1, comprising more than one probe-loaded region.

9. The polymeric particle of claim 1, wherein the particle comprises more than one encoded region.

10. The polymeric particle of claim 1, wherein the PEG hydrogel particle is polymerized from poly(ethylene glycol) diacrylate.

11. The polymeric particle of claim 1, wherein the at least one encoded region is loaded with one or more fluorescent entities.

12. The polymeric particle of claim 1, wherein the at least one probe-loaded region comprises multiple probes.

13. The polymeric particle of claim 1, wherein the probe comprises a linking chemical entity.

What is claimed is:

1. A polymeric particle comprising at least one encoded region and at least one probe-loaded region, the at least one encoded region being a distinct region from the at least one probe-loaded region, wherein the polymeric particle is a PEG hydrogel particle synthesized from a first and second monomer streams; wherein the encoded region is synthesized from the first monomer stream, and the probe-loaded region is synthesized from the second monomer stream loaded with at least one oligonucleotide probe at a concentration of between 50 μM and 150 μM, such that the probe is embedded within 14. The polymeric particle of claim 3, wherein the encoded region comprises graphical encoding, wherein the spatially patterned features allow decoding of the graphically encoded region.

15. The polymeric particle of claim 1, wherein the encoded region and the probe-loaded region are synthesized from the first and second monomers simultaneously.

16. The polymeric particle of claim 1, wherein the polymeric particle is porous.

17. The polymeric particle of claim 1, wherein the polymeric particle is a single-probe particle.

18. The polymeric particle of claim 1, wherein the probe is incorporated across a sensing region of the polymeric particle.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide probe

<400> SEQUENCE: 1
atagcagatc agcagccaga                                          20

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide probe

<400> SEQUENCE: 2
cactatgcgc aggttctcat                                          20